US008683997B2

(12) United States Patent
DeVries et al.

(10) Patent No.: US 8,683,997 B2
(45) Date of Patent: *Apr. 1, 2014

(54) PORTABLE VENTILATOR SYSTEM

(75) Inventors: Douglas F. DeVries, Kenmore, WA (US); David Boyle, Monrovia, CA (US); Michael Holmes, Corona, CA (US); Malcolm Williams, San Clemente, CA (US)

(73) Assignee: CareFusion 203, Inc., San Diego, CA (US)

( * ) Notice: Subject to any disclaimer, the term of this patent is extended or adjusted under 35 U.S.C. 154(b) by 908 days.

This patent is subject to a terminal disclaimer.

(21) Appl. No.: 11/979,142

(22) Filed: Oct. 31, 2007

(65) Prior Publication Data

US 2008/0053438 A1 Mar. 6, 2008

Related U.S. Application Data

(60) Continuation of application No. 11/445,724, filed on Jun. 2, 2006, now Pat. No. 8,297,279, which is a division of application No. 10/912,747, filed on Aug. 4, 2004, now Pat. No. 7,188,621, application No. 11/979,142, which is a continuation of application No. 11/445,762, filed on Jun. 2, 2006, which is a division of application No. 10/912,747, filed on Aug. 4, 2004, now Pat. No. 7,188,621.

(60) Provisional application No. 60/492,421, filed on Aug. 4, 2003.

(51) Int. Cl.
*A61M 16/00* (2006.01)
*H02P 5/00* (2006.01)

(52) U.S. Cl.
USPC ............. 128/204.21; 128/200.24; 128/204.18

(58) Field of Classification Search
USPC ............. 128/200.24, 203.12, 203.13, 203.14, 128/204.18, 204.21, 204.23, 206.21, 128/DIG. 7, 203.11, 205.24; 418/206.1, 418/206.5, 201.1, 201.3

See application file for complete search history.

(56) References Cited

U.S. PATENT DOCUMENTS

| 56,614 A | 7/1866 | Roots et al. |
| 587,907 A | 8/1897 | Ames et al. |

(Continued)

FOREIGN PATENT DOCUMENTS

| DE | 3238015 | 4/1984 |
| DE | 3414064 | 10/1985 |

(Continued)

OTHER PUBLICATIONS

Hinrichs, Dr. Gustavus "Introduction to General Chemistry, a Graded Course of One Hundred Lectures", *St. Louis, Mo: Hinrichs*, (1897),87-89.

(Continued)

*Primary Examiner* — Annette Dixon
(74) *Attorney, Agent, or Firm* — McDermott Will & Emery LLP

(57) ABSTRACT

A portable ventilator uses a ROOTS-type blower as a compressor to reduce both the size and power consumption of the ventilator. Various functional aspects of the ventilator are delegated to multiple subassemblies having dedicated controllers and software that interact with a ventilator processor to provide user interface functions, exhalation control and flow control servos, and monitoring of patient status. The ventilator overcomes noise problems through the use of noise reducing pressure compensating orifices on the ROOTS-type blower housing and multiple baffling chambers. The ventilator is configured with a highly portable form factor, and may be used as a stand-alone device or as a docked device having a docking cradle with enhanced interface and monitoring capabilities.

24 Claims, 21 Drawing Sheets

(56) References Cited

U.S. PATENT DOCUMENTS

| | | | |
|---|---|---|---|
| 1,769,153 A | 7/1930 | Meyer | |
| 2,014,932 A | 9/1935 | Hallett | 230/141 |
| 2,787,999 A | 4/1957 | Bennett | 128/30 |
| 3,089,638 A | 5/1963 | Rose | 230/141 |
| 3,094,274 A | 6/1963 | Thompson | 230/224 |
| 3,371,856 A | 3/1968 | Thelen et al. | 230/141 |
| 3,459,395 A | 8/1969 | Scotto | 248/20 |
| 3,658,443 A | 4/1972 | Fumagalli | 417/384 |
| 3,865,523 A * | 2/1975 | Baehr | 418/201.1 |
| 3,905,362 A | 9/1975 | Eyrick et al. | |
| 3,941,206 A | 3/1976 | Halter | 181/50 |
| 4,080,103 A | 3/1978 | Bird | 417/3 |
| 4,096,858 A | 6/1978 | Eyrick et al. | |
| 4,121,578 A | 10/1978 | Torzala | 128/142 R |
| 4,182,599 A | 1/1980 | Eyrick et al. | |
| 4,215,977 A | 8/1980 | Weatherston | 418/1 |
| 4,220,219 A | 9/1980 | Flugger | 181/265 |
| 4,227,869 A | 10/1980 | Eriksson | 418/206 |
| 4,239,039 A | 12/1980 | Thompson | 128/205.24 |
| 4,248,194 A | 2/1981 | Drutchas et al. | |
| 4,257,453 A | 3/1981 | Kohnke | |
| 4,267,899 A | 5/1981 | Wagner et al. | 181/272 |
| 4,323,064 A | 4/1982 | Hoenig et al. | 128/204.21 |
| 4,448,192 A | 5/1984 | Stawitcke et al. | 128/204.26 |
| 4,455,132 A | 6/1984 | Messori | 418/206 |
| 4,495,947 A | 1/1985 | Motycka | 128/205.14 |
| 4,564,345 A | 1/1986 | Mueller | 418/206 |
| 4,595,349 A | 6/1986 | Preston et al. | 418/206 |
| 4,609,335 A | 9/1986 | Uthoff, Jr. | 418/201 |
| 4,637,439 A | 1/1987 | Jeans | |
| 4,656,553 A | 4/1987 | Brown | |
| 4,666,384 A | 5/1987 | Kaga et al. | 418/150 |
| 4,673,058 A | 6/1987 | Roberts et al. | 181/266 |
| 4,684,330 A | 8/1987 | Andersson et al. | 417/360 |
| 4,686,999 A | 8/1987 | Snyder et al. | 128/716 |
| 4,702,240 A | 10/1987 | Choui | 128/204.18 |
| 4,768,934 A | 9/1988 | Soeters, Jr. | 418/1 |
| 4,781,541 A | 11/1988 | Sohler et al. | 417/312 |
| 4,794,922 A | 1/1989 | DeVries | 128/204.18 |
| 4,844,044 A | 7/1989 | McGovern | 123/559.1 |
| 4,846,302 A | 7/1989 | Hetherington | 181/243 |
| 4,867,151 A | 9/1989 | Bird | 128/201.17 |
| 4,897,583 A | 1/1990 | Rees | |
| 4,938,670 A | 7/1990 | Lee | 418/150 |
| 4,957,107 A | 9/1990 | Sipin | 128/204.21 |
| 4,975,032 A | 12/1990 | Arai et al. | 418/150 |
| 5,040,959 A | 8/1991 | Fukagawa | 418/150 |
| 5,056,995 A | 10/1991 | Tamura et al. | 418/201.1 |
| 5,131,829 A | 7/1992 | Hampton | 418/189 |
| 5,145,349 A | 9/1992 | McBurnett | 418/206 |
| 5,152,684 A | 10/1992 | Steffens | 418/150 |
| 5,161,525 A | 11/1992 | Kimm et al. | 128/204.26 |
| 5,211,170 A | 5/1993 | Press | 128/204.18 |
| 5,222,148 A | 6/1993 | Yuan | 381/71 |
| 5,237,987 A | 8/1993 | Anderson et al. | 128/204.18 |
| 5,239,994 A | 8/1993 | Atkins | 128/204.18 |
| 5,253,486 A | 10/1993 | Sugahara et al. | |
| 5,335,651 A | 8/1994 | Foster et al. | 128/202.13 |
| 5,350,888 A | 9/1994 | Sager, Jr. et al. | 181/247 |
| 5,384,527 A | 1/1995 | Rozman et al. | |
| 5,388,575 A * | 2/1995 | Taube | 128/204.23 |
| 5,398,676 A | 3/1995 | Press et al. | 128/204.23 |
| 5,428,276 A | 6/1995 | Carobolante et al. | |
| 5,430,362 A | 7/1995 | Carr et al. | |
| 5,439,358 A | 8/1995 | Weinbrecht | 418/15 |
| 5,452,714 A * | 9/1995 | Anderson et al. | 128/205.11 |
| 5,461,293 A | 10/1995 | Rozman et al. | |
| 5,493,200 A | 2/1996 | Rozman et al. | |
| 5,495,162 A | 2/1996 | Rozman et al. | |
| 5,495,163 A | 2/1996 | Rozman et al. | |
| 5,542,416 A | 8/1996 | Chalvignac | 128/204.23 |
| 5,577,152 A | 11/1996 | Chen | 388/804 |
| 5,582,163 A | 12/1996 | Bonassa | 128/204.26 |
| 5,632,270 A | 5/1997 | O'Mahony et al. | 128/204.24 |
| 5,638,600 A | 6/1997 | Rao et al. | 29/888.02 |
| 5,664,563 A | 9/1997 | Schroeder et al. | 128/204.25 |
| 5,687,717 A | 11/1997 | Halpern et al. | 128/630 |
| 5,694,926 A | 12/1997 | DeVries et al. | 128/205.24 |
| 5,701,883 A | 12/1997 | Hete et al. | 128/204.26 |
| 5,702,240 A | 12/1997 | O'Neal et al. | 418/9 |
| 5,760,348 A | 6/1998 | Heuser | 181/272 |
| 5,763,792 A | 6/1998 | Kullik | 73/861.53 |
| 5,783,782 A | 7/1998 | Sterrett et al. | 181/272 |
| 5,799,652 A * | 9/1998 | Kotliar | 128/205.11 |
| 5,823,186 A | 10/1998 | Rossen et al. | 128/204.21 |
| 5,831,223 A | 11/1998 | Kesselring | 181/227 |
| 5,868,133 A | 2/1999 | DeVries et al. | 128/204.21 |
| 5,871,465 A | 2/1999 | Vasko | |
| 5,880,586 A | 3/1999 | Dukart et al. | |
| 5,881,722 A | 3/1999 | DeVries et al. | 128/204.21 |
| 5,918,597 A | 7/1999 | Jones et al. | 128/205.18 |
| 5,931,159 A | 8/1999 | Suzuki et al. | 128/204.18 |
| 5,944,501 A | 8/1999 | Yokoi | 418/181 |
| 5,996,731 A | 12/1999 | Czabala et al. | |
| 6,009,871 A | 1/2000 | Kiske et al. | 128/204.21 |
| 6,065,944 A * | 5/2000 | Cobb | 417/394 |
| 6,070,576 A * | 6/2000 | Banucci et al. | 128/203.28 |
| 6,076,523 A | 6/2000 | Jones et al. | 128/205.11 |
| 6,099,277 A | 8/2000 | Patel et al. | 418/1 |
| 6,102,038 A | 8/2000 | DeVries | 128/204.24 |
| 6,125,844 A | 10/2000 | Samiotes | 128/200.23 |
| 6,152,129 A | 11/2000 | Berthon-Jones | 128/200.24 |
| 6,152,135 A | 11/2000 | DeVries et al. | 128/205.24 |
| 6,155,257 A | 12/2000 | Lurie et al. | 128/204.23 |
| 6,158,430 A | 12/2000 | Pfeiffer et al. | 128/202.27 |
| 6,158,434 A | 12/2000 | Lugtigheid et al. | 128/204.22 |
| 6,164,412 A | 12/2000 | Allman | 181/272 |
| 6,176,693 B1 * | 1/2001 | Conti | 418/180 |
| 6,237,592 B1 | 5/2001 | Surjadi et al. | |
| 6,239,564 B1 | 5/2001 | Boe et al. | |
| 6,247,906 B1 | 6/2001 | Pijanowski | |
| 6,279,574 B1 | 8/2001 | Richardson et al. | 128/204.18 |
| 6,279,576 B1 * | 8/2001 | Lambert | 128/205.28 |
| 6,283,246 B1 | 9/2001 | Nishikawa | 181/255 |
| 6,305,372 B1 | 10/2001 | Servidio | 128/204.21 |
| 6,349,724 B1 | 2/2002 | Burton et al. | |
| 6,354,558 B1 | 3/2002 | Li | 248/615 |
| 6,412,483 B1 | 7/2002 | Jones et al. | 128/205.11 |
| 6,468,222 B1 | 10/2002 | Mault et al. | |
| 6,474,960 B1 | 11/2002 | Hansmann | 417/363 |
| 6,479,987 B1 | 11/2002 | Marx et al. | |
| 6,484,719 B1 | 11/2002 | Berthon-Jones | 128/204.23 |
| 6,526,970 B2 | 3/2003 | DeVries et al. | 128/204.21 |
| 6,543,449 B1 | 4/2003 | Woodring et al. | 128/204.18 |
| 6,558,137 B2 | 5/2003 | Tomell et al. | 417/312 |
| 6,564,798 B1 | 5/2003 | Jalde | 128/205.24 |
| 6,571,792 B1 | 6/2003 | Hendrickson et al. | 128/203.12 |
| 6,571,796 B2 | 6/2003 | Banner et al. | 128/204.26 |
| 6,591,835 B1 | 7/2003 | Blanch | 128/204.25 |
| 6,615,446 B2 | 9/2003 | Noreen et al. | |
| 6,615,831 B1 | 9/2003 | Tuitt et al. | 128/204.18 |
| 6,619,286 B2 | 9/2003 | Patel | 128/204.26 |
| 6,619,325 B2 | 9/2003 | Gray, Jr. | |
| 6,626,175 B2 | 9/2003 | Jafari et al. | 128/204.21 |
| 6,629,525 B2 | 10/2003 | Hill et al. | 128/202.26 |
| 6,629,531 B2 | 10/2003 | Gleason et al. | 128/205.25 |
| 6,629,934 B2 | 10/2003 | Mault et al. | 600/538 |
| 6,631,716 B1 | 10/2003 | Robinson et al. | 128/204.21 |
| 6,637,430 B1 | 10/2003 | Voges et al. | 128/200.14 |
| 6,651,658 B1 | 11/2003 | Hill et al. | 128/204.23 |
| 6,666,209 B2 | 12/2003 | Bennett et al. | 128/200.24 |
| 6,672,300 B1 | 1/2004 | Grant | 124/204.26 |
| 6,691,702 B2 | 2/2004 | Appel et al. | 128/202.26 |
| 6,691,707 B1 | 2/2004 | Gunaratnam et al. | 128/206.21 |
| 6,708,690 B1 | 3/2004 | Hete et al. | 128/204.18 |
| 6,745,770 B2 | 6/2004 | McAuliffe et al. | 128/205.24 |
| 6,752,240 B1 | 6/2004 | Schlagenhaft | 181/249 |
| 6,764,534 B2 | 7/2004 | McCombs et al. | 96/111 |
| 6,770,037 B2 | 8/2004 | Sullivan et al. | 600/529 |
| 6,782,888 B1 | 8/2004 | Friberg et al. | 128/204.18 |
| 6,802,225 B2 | 10/2004 | Shahar et al. | 73/861.52 |
| 6,820,618 B2 | 11/2004 | Banner et al. | 128/204.23 |
| 6,837,260 B1 | 1/2005 | Kuehn | 137/315.01 |
| 6,877,511 B2 | 4/2005 | DeVries et al. | 128/204.26 |

(56) References Cited

U.S. PATENT DOCUMENTS

| | | | |
|---|---|---|---|
| 6,907,373 B2 | 6/2005 | Walter et al. | |
| 6,968,842 B1 | 11/2005 | Truschel et al. | 128/204.18 |
| 6,979,181 B1 | 12/2005 | Kidd | |
| 7,004,908 B2 | 2/2006 | Sullivan et al. | 600/529 |
| 7,011,092 B2 | 3/2006 | McCombs et al. | 128/205.12 |
| 7,032,589 B2 | 4/2006 | Kerechanin et al. | 128/200.24 |
| 7,063,084 B2 | 6/2006 | McDonald | 128/200.28 |
| 7,066,178 B2 | 6/2006 | Gunaratnam et al. | 128/206.21 |
| 7,066,985 B2 | 6/2006 | Deane et al. | 95/96 |
| 7,073,499 B1 | 7/2006 | Reinhold et al. | 128/200.18 |
| 7,086,366 B1 | 8/2006 | Killion | 123/192.2 |
| 7,118,536 B2 | 10/2006 | Haberland et al. | 600/538 |
| 7,121,276 B2 | 10/2006 | Jagger et al. | 128/201.21 |
| 7,168,429 B2 | 1/2007 | Matthews et al. | 128/204.21 |
| 7,171,963 B2 | 2/2007 | Jagger et al. | 128/201.21 |
| 7,183,681 B2 | 2/2007 | Segawa et al. | 310/68 B |
| 7,188,621 B2 | 3/2007 | DeVries et al. | 128/204.21 |
| 7,225,809 B1 | 6/2007 | Bowen et al. | 128/204.21 |
| 7,226,280 B1 | 6/2007 | Yokoi | 418/206.4 |
| 7,329,304 B2 | 2/2008 | Bliss et al. | 95/12 |
| 7,331,342 B2 | 2/2008 | Spearman et al. | 128/203.14 |
| 7,335,243 B2 | 2/2008 | Homan et al. | 55/385.2 |
| 7,351,034 B2 | 4/2008 | Cens et al. | 416/61 |
| 7,368,005 B2 | 5/2008 | Bliss et al. | 96/121 |
| 2001/0044588 A1 | 11/2001 | Mault | 600/549 |
| 2002/0134378 A1 | 9/2002 | Finnegan et al. | 128/200.24 |
| 2003/0024529 A1 | 2/2003 | Beizndtsson et al. | |
| 2003/0057904 A1 | 3/2003 | Sacher | 318/268 |
| 2003/0208113 A1 | 11/2003 | Mault et al. | 600/316 |
| 2004/0015364 A1 | 1/2004 | Sulc | |
| 2004/0040563 A1 | 3/2004 | Chu et al. | |
| 2004/0061996 A1 | 4/2004 | Kamphuis et al. | |
| 2004/0074495 A1 | 4/2004 | Wickham et al. | 128/204.18 |
| 2004/0147818 A1 | 7/2004 | Levy et al. | 600/300 |
| 2004/0190236 A1 | 9/2004 | Medica et al. | |
| 2004/0211422 A1 | 10/2004 | Arcilla et al. | 128/204.19 |
| 2004/0221854 A1 | 11/2004 | Hete et al. | 128/207.16 |
| 2004/0226562 A1 | 11/2004 | Bordewick | 128/204.23 |
| 2005/0112013 A1 | 5/2005 | DeVries et al. | 418/206.1 |
| 2005/0124866 A1 | 6/2005 | Elaz et al. | 600/301 |
| 2005/0166921 A1 | 8/2005 | DeVries et al. | 128/204.21 |
| 2005/0188991 A1 | 9/2005 | Sun et al. | 128/204.23 |
| 2005/0241642 A1 | 11/2005 | Krzysztofik | 128/206.15 |
| 2006/0065672 A1 | 3/2006 | LeCourt et al. | 222/3 |
| 2006/0069326 A1 | 3/2006 | Heath | 601/41 |
| 2006/0070624 A1 | 4/2006 | Kane et al. | 128/204.23 |
| 2006/0124128 A1 | 6/2006 | Deane et al. | 128/204.21 |
| 2006/0144396 A1 | 7/2006 | DeVries et al. | 128/204.21 |
| 2006/0144399 A1 | 7/2006 | Davidowski et al. | 128/205.21 |
| 2006/0144405 A1 | 7/2006 | Gunaratnam et al. | 128/206.21 |
| 2006/0150973 A1 | 7/2006 | Chalvignac | 128/214.21 |
| 2006/0174871 A1 | 8/2006 | Jagger et al. | 128/201.21 |
| 2006/0174872 A1 | 8/2006 | Jagger et al. | 128/201.21 |
| 2006/0174874 A1 | 8/2006 | Jagger et al. | 128/201.21 |
| 2006/0174875 A1 | 8/2006 | Jagger et al. | 128/201.21 |
| 2006/0174877 A1 | 8/2006 | Jagger et al. | 128/201.21 |
| 2006/0174878 A1 | 8/2006 | Jagger et al. | 128/201.21 |
| 2006/0174880 A1 | 8/2006 | Jagger et al. | 128/201.25 |
| 2006/0174881 A1 | 8/2006 | Jagger et al. | 128/201.25 |
| 2006/0174882 A1 | 8/2006 | Jagger et al. | 128/201.25 |
| 2006/0201503 A1 | 9/2006 | Breen | 128/204.18 |
| 2006/0213518 A1 | 9/2006 | DeVries et al. | 128/204.21 |
| 2006/0249149 A1 | 11/2006 | Meier et al. | 128/204.18 |
| 2006/0266355 A1 | 11/2006 | Misholi | 128/204.22 |
| 2006/0283450 A1 | 12/2006 | Shissler et al. | 128/204.21 |
| 2007/0044799 A1 | 3/2007 | Hete et al. | 128/205.11 |
| 2007/0062529 A1 | 3/2007 | Choncholas et al. | 128/204.22 |
| 2007/0062532 A1 | 3/2007 | Choncholas | 128/204.23 |
| 2007/0068526 A1 | 3/2007 | Lang et al. | 128/204.22 |
| 2007/0079826 A1 | 4/2007 | Kramer et al. | 128/200.14 |
| 2007/0113843 A1 | 5/2007 | Hughes | 128/200.24 |
| 2007/0113849 A1 | 5/2007 | Matthews et al. | 128/204.22 |
| 2007/0169776 A1 | 7/2007 | Kepler et al. | 128/200.23 |
| 2007/0181127 A1 | 8/2007 | Jin et al. | 128/204.21 |
| 2007/0193580 A1 | 8/2007 | Feldhahn et al. | 128/204.18 |
| 2007/0215146 A1 | 9/2007 | Douglas et al. | 128/200.24 |
| 2007/0221224 A1 | 9/2007 | Pittman et al. | 128/204.22 |
| 2007/0235030 A1 | 10/2007 | Teetzel et al. | 128/205.12 |
| 2007/0265877 A1 | 11/2007 | Rice et al. | 705/2 |
| 2007/0277825 A1 | 12/2007 | Bordewick et al. | 128/204.23 |
| 2008/0000474 A1 | 1/2008 | Jochle et al. | 128/204.18 |
| 2008/0029096 A1 | 2/2008 | Kollmeyer et al. | 128/204.21 |
| 2008/0035149 A1 | 2/2008 | Sutton | 128/205.24 |
| 2008/0039701 A1 | 2/2008 | Ali et al. | 600/301 |
| 2008/0051674 A1* | 2/2008 | Davenport et al. | 600/561 |
| 2008/0066739 A1 | 3/2008 | LeMahieu et al. | 128/200.14 |
| 2008/0078395 A1 | 4/2008 | Ho et al. | 128/205.24 |
| 2008/0099017 A1 | 5/2008 | Bordewick et al. | 128/204.21 |
| 2008/0110455 A1 | 5/2008 | Dunsmore et al. | 128/200.24 |
| 2008/0110458 A1 | 5/2008 | Srinivasan et al. | 128/203.26 |
| 2008/0110462 A1 | 5/2008 | Chekal et al. | 128/204.26 |
| 2008/0127976 A1 | 6/2008 | Acker et al. | 128/204.18 |

FOREIGN PATENT DOCUMENTS

| | | |
|---|---|---|
| DE | 3620792 | 12/1987 |
| DE | 19817356 | 10/1999 |
| EP | 0239026 | 9/1987 |
| EP | 0521709 | 1/1993 |
| EP | 0938909 | 9/1999 |
| EP | 1130761 | 9/2001 |
| EP | 1243282 | 9/2002 |
| FR | 2875891 | 9/2004 |
| GB | 1387841 | 3/1975 |
| GB | 1447091 | 8/1976 |
| GB | 2157370 | 10/1985 |
| JP | 08-010331 | 1/1996 |
| JP | 2001050774 | 2/2001 |
| JP | 2003124986 | 4/2003 |
| WO | WO 89/10768 | 11/1989 |
| WO | WO 92/11054 | 7/1992 |
| WO | WO 96/11717 | 4/1996 |
| WO | WO 97/11522 | 3/1997 |
| WO | WO 97/15343 | 5/1997 |
| WO | WO 99/64825 | 12/1999 |
| WO | WO 00/45883 | 8/2000 |
| WO | WO 02/11861 | 2/2002 |
| WO | WO 2004/040745 | 5/2004 |
| WO | WO-2005/013879 | 2/2005 |

OTHER PUBLICATIONS

Office Action, CA Application No. 2,574,018, mailed May 9, 2012, 4 pages.

Extended European Search Report, EP Application No. 07809783.9, Mailed Jun. 6, 2012, 8 pages.

Office Action, JP Application No. 2009-519444, mailed Jan. 10, 2012, 3 pages.

M.L. Munjal, "Acoustics of Ducts and Mufflers," John Wiley & Sons, 1987, chapter 8.

Eaton, "Why an Eaton Supercharger?" www.eaton.com/supercharger/whysuper.html.

* cited by examiner

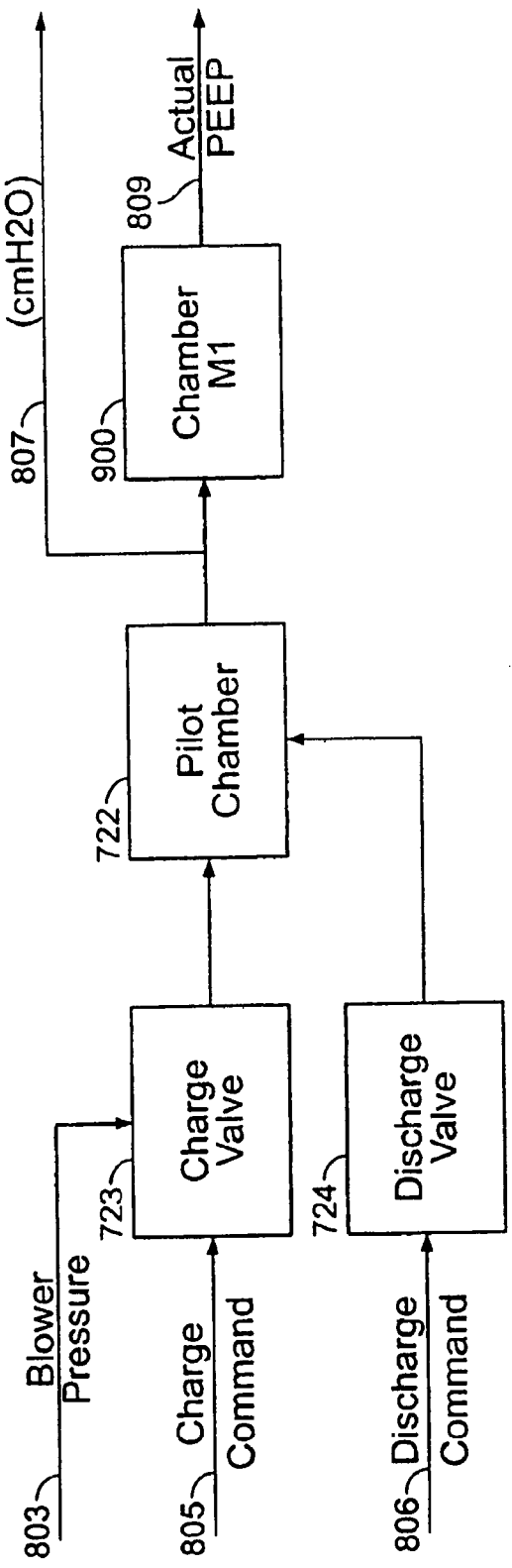
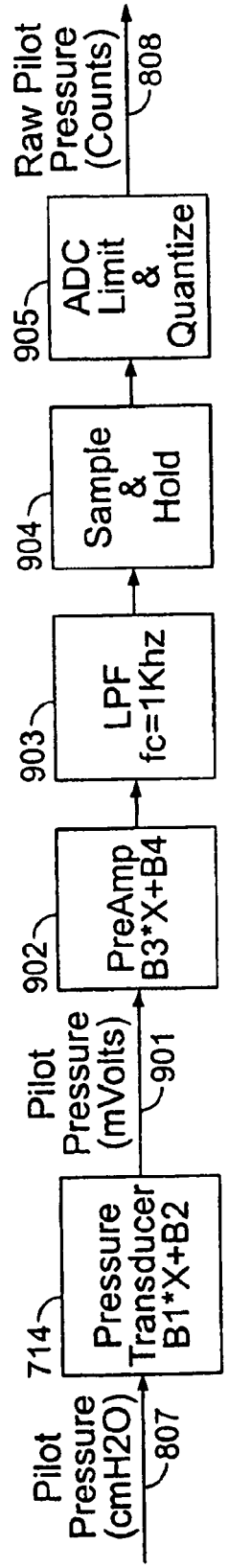
FIG. 9A
FIG. 9B

PORTABLE VENTILATOR SYSTEM

CROSS-REFERENCE TO RELATED APPLICATIONS

This application claims priority under 35 USC §120 to and is a continuation of U.S. patent application entitled, Portable Ventilator System, filed Jun. 2, 2006, having a Ser. No. 11/445,724, now U.S. Pat. No. 8,297,279, the disclosure of which is hereby incorporated by reference in its entirety. This application also claims priority to and is a continuation of U.S. patent application entitled, Portable Ventilator System, filed Jun. 2, 2006, having a Ser. No. 11/445,762, now U.S. Pat. No. 8,627,819, the disclosure of which is hereby incorporated by reference in its entirety. U.S. application Ser. Nos. 11/445,724 and 11/445,762 claimed priority and are divisionals of U.S. Pat. No. 7,188,621, filed on Aug. 4, 2004, the disclosure of which is hereby incorporated by reference in its entirety. U.S. application Ser. Nos. 11/445,724, 11/445,762 and U.S. Pat. No. 7,188,621 claimed priority from expired U.S. Provisional Patent Application Ser. No. 60/492,421, filed Aug. 4, 2003, the disclosure of which is hereby incorporated by reference in its entirety. This application also claims priority from U.S. Pat. No. 7,188,621 and U.S. provisional application 60/492,421. This application also cross-references U.S. application Ser. No. 10/985,528 filed on Nov. 10, 2004, U.S. Pat. No. 7,527,053 filed on Mar. 23, 2005, U.S. application Ser. No. 11/234,636 filed on Sep. 23, 2005, U.S. application Ser. No. 11/486,346 filed on Jul. 13, 2006, and U.S. application Ser. No. 11/712,929 filed on Mar. 1, 2007, all of which claim the benefit of U.S. Pat. No. 7,188,621, the disclosures of which are all hereby incorporated by reference in their entirety.

FIELD OF THE INVENTION

This invention relates to the field of medical ventilators, and more specifically to a self-contained portable ventilator.

A portion of the disclosure of this patent document contains material which is subject to copyright protection. The copyright owner has no objection to the facsimile reproduction by anyone of the patent document or the patent disclosure, as it appears in the Patent and Trademark Office file or records, but otherwise reserves all copyrights associated with this document.

BACKGROUND OF THE INVENTION

Ventilators for patients requiring breathing assistance have traditionally been large, heavy, power-hungry devices that have provided little if any mobility to a patient. Recent advances in compressor technology, such as those described in U.S. Pat. No. 6,152,135 issued to DeVries et al., have allowed a reduction in size and power requirements of ventilators, for the first time allowing the manufacture of ventilators that were able to provide a limited degree of self-contained portability. Outfitted with battery packs, these portable ventilators could be attached to a wheel chair, providing a patient the ability to move about for a limited amount of time without having the ventilator connected to a power supply main.

Ventilators of the prior art have become smaller and more transportable while maintaining the ability to deliver complex breath modes by typically using low pressure rotary drag compressors as the breath delivery mechanism. The drag compressors may either be variable speed or constant speed. Variable speed ventilator compressors operate by rapidly accelerating from a standstill to provide inhalation assistance (inspiration) to a patient, then decelerate rapidly to allow a patient to exhale. The rapid acceleration and deceleration of prior art variable speed compressor ventilators require the compressor's drive circuitry to handle very high currents, necessitating bulky and expensive power systems and considerable standby battery power when the ventilator is not connected to a power main.

Constant speed compressors do not need the bulky power systems of variable-speed compressors, but have inherent inefficiencies because the compressor continues to run and consume power even at times when no air is being supplied to the patient (such as during exhalation). The power consumption can be reduced by recirculating the compressor's output air flow to the compressor's intake during exhalation. However, even the reduced power consumed significantly reduces the amount of time the ventilator can be operated from on-board battery power.

SUMMARY OF THE INVENTION

The present invention comprises a portable ventilator that uses a small, low-inertia, high-speed, high-efficiency ROOTS-type blower in variable-speed mode. ROOTS-type blowers are known for high-efficiency and small size. However, they are inherently noisy, and have in the past not been suited for use in medical ventilators, where excessive noise is disruptive to patients, who often require around-the-clock breathing assistance. The ventilator of the present invention overcomes the noise problems of prior art ROOTS-type blowers through the combined use of novel noise reducing pressure compensating orifices on the ROOTS-type blower housing and multiple baffling chambers within the ventilator's housing. The use of a ROOTS-type compressor in a variable-speed mode, together with specially configured flow control and power systems, reduces both the size and power consumption of the ventilator as a whole. Embodiments of the invention provide full ventilator functionality, including the capability of operating in both volume and pressure control modes, in small, truly portable units that for the first time provide real mobility to patients. In one embodiment, the ventilator is a portable, self-contained ventilator that approximates the size of a small laptop computer while providing several hours of battery powered, full-service breathing assistance.

In one or more embodiments of the invention, the ventilator employs a heavier ROOTS-type blower with greater inertia in constant speed mode. The extra ordinary efficiency of the ROOTS-type blower permits size and weight reductions to a degree previously unattainable in a full featured ventilator capable of delivering complex breath modes.

BRIEF DESCRIPTION OF THE DRAWINGS

FIG. 9A is a block diagram of a mechanical assembly portion of an exhalation servo control system in accordance with one or more embodiments of the invention.

FIG. 9B is a block diagram of an electronic assembly portion of an exhalation servo control system in accordance with one or more embodiments of the invention.

DETAILED DESCRIPTION

A portable ventilator system is described. In the following description, numerous specific details, such as physical dimensions for one or more embodiments, are set forth to provide a more thorough description of the invention. It will be apparent, however, to one skilled in the art, that the invention may be practiced without these specific details. In other instances, well known features have not been described in detail so as not to obscure the invention.

Embodiments of the invention implement a portable ventilator that uses a ROOTS-type blower operating in a variable speed mode as the breath delivery mechanism. The efficiencies and reduced size requirements resulting from the use of a ROOTS-type blower, together with novel sound muffling techniques and electronic control systems, allow the ventilator to be reduced in size to be comparable to a palmtop computer. Weight and power consumption may likewise be reduced. The ventilator of the present invention provides true, extended mobility to patients who require continuous breathing assistance, facilitating a significant improvement in their quality of life.

I. Embodiment of Ventilator System with Portable Ventilator, Docking Cradle and Monitor In one or more embodiments of the invention, a portable ventilator system includes a portable ventilator, a docking cradle and a monitor. The portable ventilator is preferably, though not necessarily, a small, lightweight, self-contained life support device that is highly portable. In stationary applications, the portable ventilator may be placed into a docking cradle that acts as a simple structural support, possibly including a power supply and/or recharging system, or that expands the portable ventilators interface capabilities. For example, the docking cradle may also include a graphics monitor for enhanced display capabilities.

A. Portable Ventilator Enclosure

In one or more embodiments, the portable ventilator may be packaged within a molded enclosure. In some embodiments, the enclosure is co-molded with a soft rubber boot. Preferably, though not necessarily, the enclosure is configured to have a relatively compact form factor. For example, in one embodiment, an enclosure that is 10".times.6".times.2" may contain the apparatus needed for a patient to receive proper ventilator support from a highly portable unit. Other embodiments may use enclosures with varying form factors.

Figure 1:
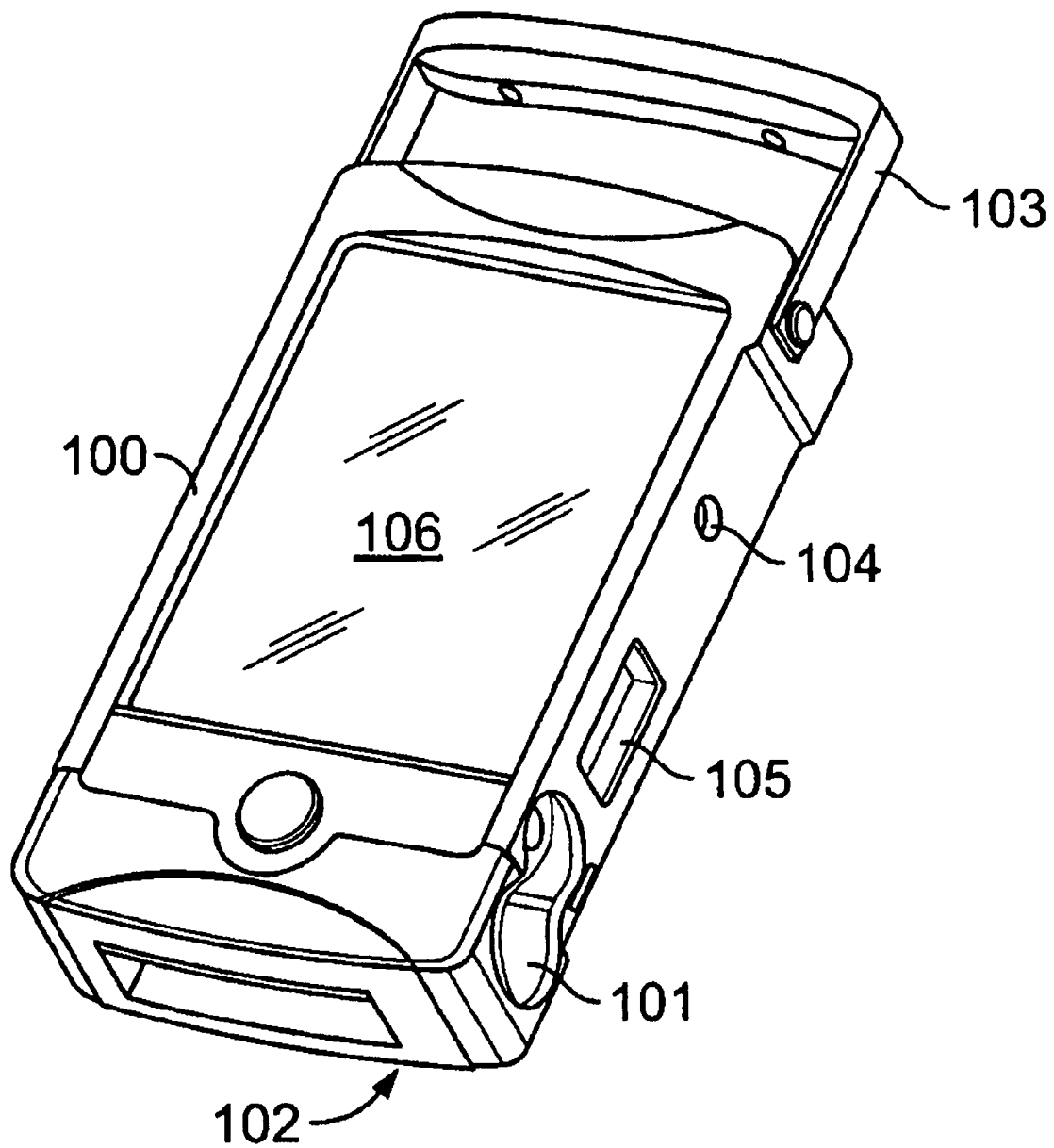
FIG. 1 is a perspective view of the front face of a portable ventilator in accordance with one or more embodiments of the invention.

FIG. 1 is a diagram illustrating a perspective view of the front face of a portable ventilator, in accordance with one or more embodiments of the invention. In the illustrated embodiment, the pneumatic connections 101 may be made on the left and right sides, e.g., below the centerline of ventilator enclosure 100. Electrical interconnects 102 may be made on the lower edge of the backside of enclosure 100 (e.g., to provide a cradle interface). The electrical interconnects may also be made on the left and/or right sides of enclosure 100, e.g., above the centerline.

The ventilator enclosure may include a user interface 106. For example, user interface 106 may be implemented relatively inexpensively in one embodiment with LEDs and a membrane switch panel. Another embodiment may implement a graphical user interface 106 using a color LCD and touch screen.

In one or more embodiments, the top of ventilator enclosure 100 may include a collapsible handle 103 that acts as a table stand when folded and collapses flush against the enclosure. Hand/shoulder strap connection points 104 may be built into enclosure 100. One or more embodiments may also implement a low-profile, dovetail-style mounting mechanism on the rear of enclosure 100 to facilitate pole, wall or bed-rail mounting without interfering with non-mounted desktop applications.

In one or more embodiments, battery port 105 may be provided on enclosure 100 to accommodate an internal, removable battery pack. Battery port 105 is preferably equipped with a latch and eject mechanism to insure a reliable connection when in use, and easy swapping of the removable battery pack, even when the enclosure is seated in a cradle (described below). Enclosure 100 may be designed to drop into a docking cradle for raised support and/or to establish a connection between the portable ventilator and cradle electronics. An embodiment of a docking cradle is described below.

B. Docking Cradle and Monitor

Figure 2A:
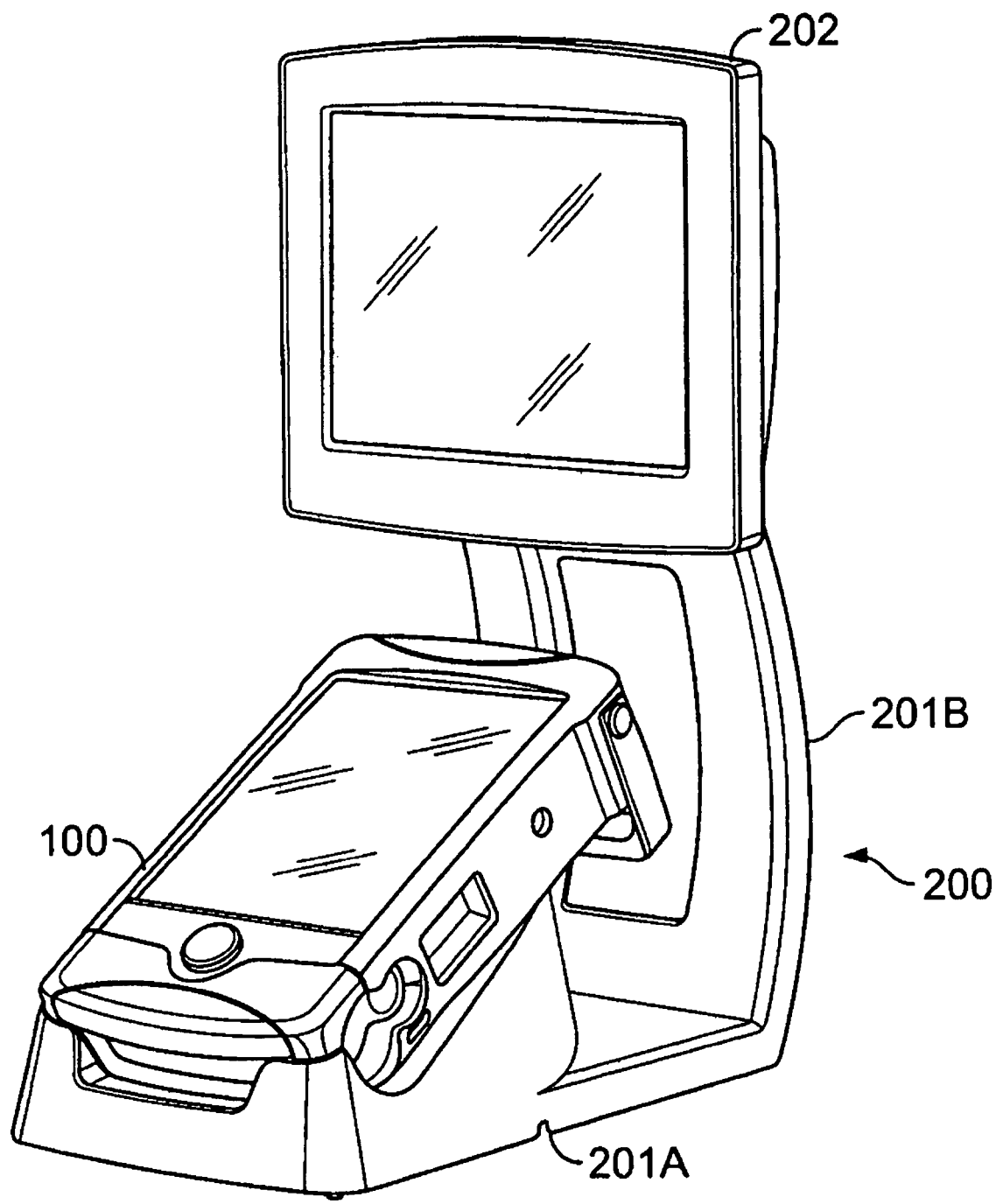
FIG. 2A is perspective view of the front of a ventilator system including a portable ventilator, a docking cradle and a ventilator monitor, in accordance with one or more embodiments of the invention.
Figure 2B:
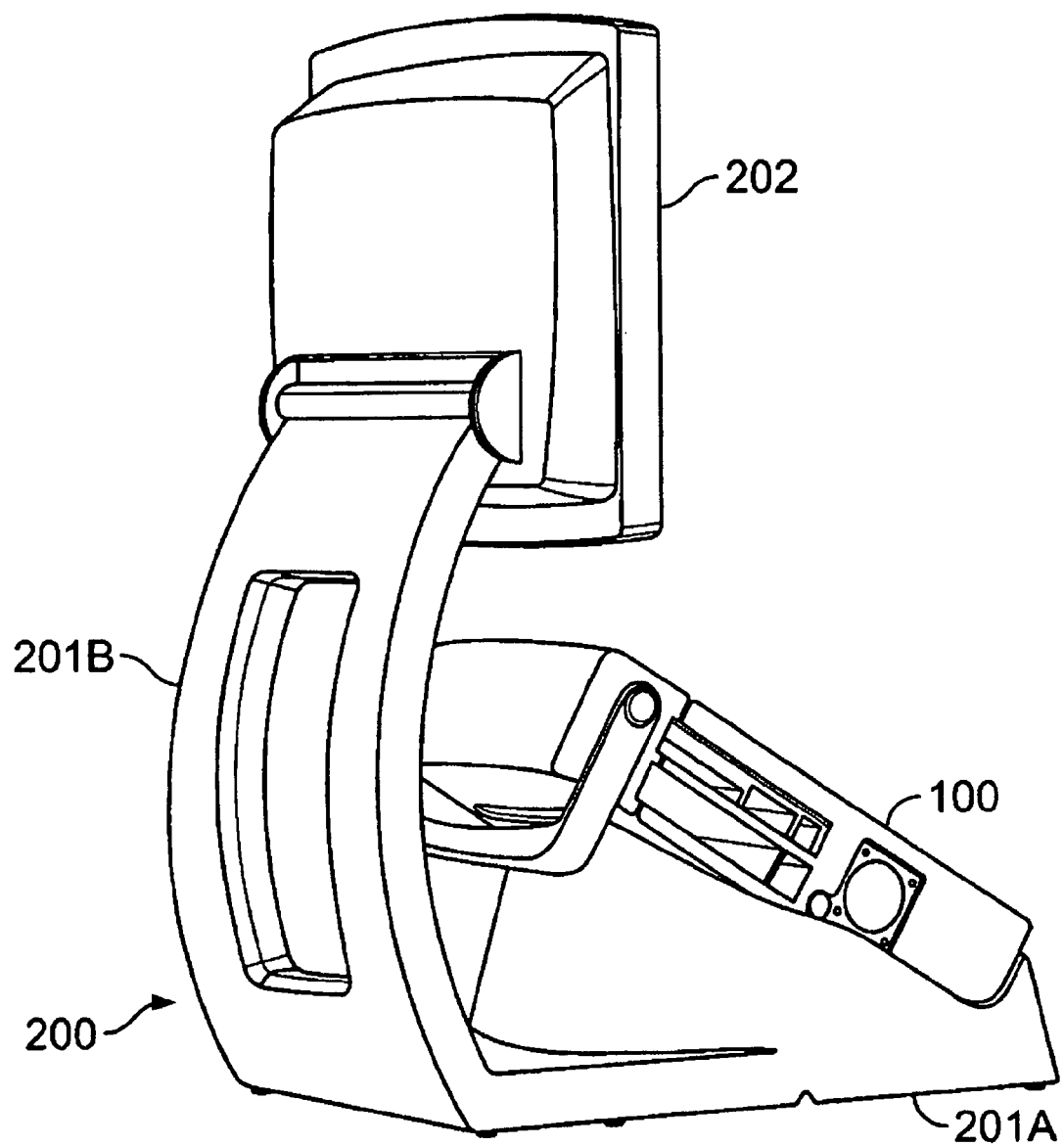
FIG. 2B is a perspective view of the rear of the ventilator system of FIG. 2A.

FIGS. 2A and 2B provide a perspective views of the front and rear of a portable ventilator system, comprising a portable ventilator, a docking cradle and a monitor, in accordance with one or more embodiments of the invention. As shown, docking cradle 200 may include a base 201A and a cradle arm 201B. A monitor 202 may be attached to arm 201B to provide a display for expanded ventilator monitoring capabilities. Portable ventilator enclosure 100 is shown docked into base 201A of cradle 200.

In one or more embodiments, base 201A is designed to function as a simple table stand, without any internal power or logic components. However, in most embodiments, internal electronics are included to provide an intelligent docking station capable of supplying power and expanding the interface capabilities of the portable ventilator. In the latter case, base 201A provides an electrical interconnection with the docked ventilator, e.g., through the lower, back edge of the ventilator. Arm 201B may be removably attached to base 201A to provide a support for the optional monitor 202. Power and data cables between electronics in the cradle base 201A and monitor 202 may be hidden within the structure of arm 201B.

Cradle 200 may include a mechanical interlock to ensure that the docked ventilator cannot fall out. As with the ventilator enclosure 100, cradle 200 may also incorporate a dovetail-style mounting mechanism to facilitate wall or bed-rail mounting. The docking cradle 200 and monitor 202 may each contain injection molded components.

C. Ventilator System Functional Architecture

Figure 3:
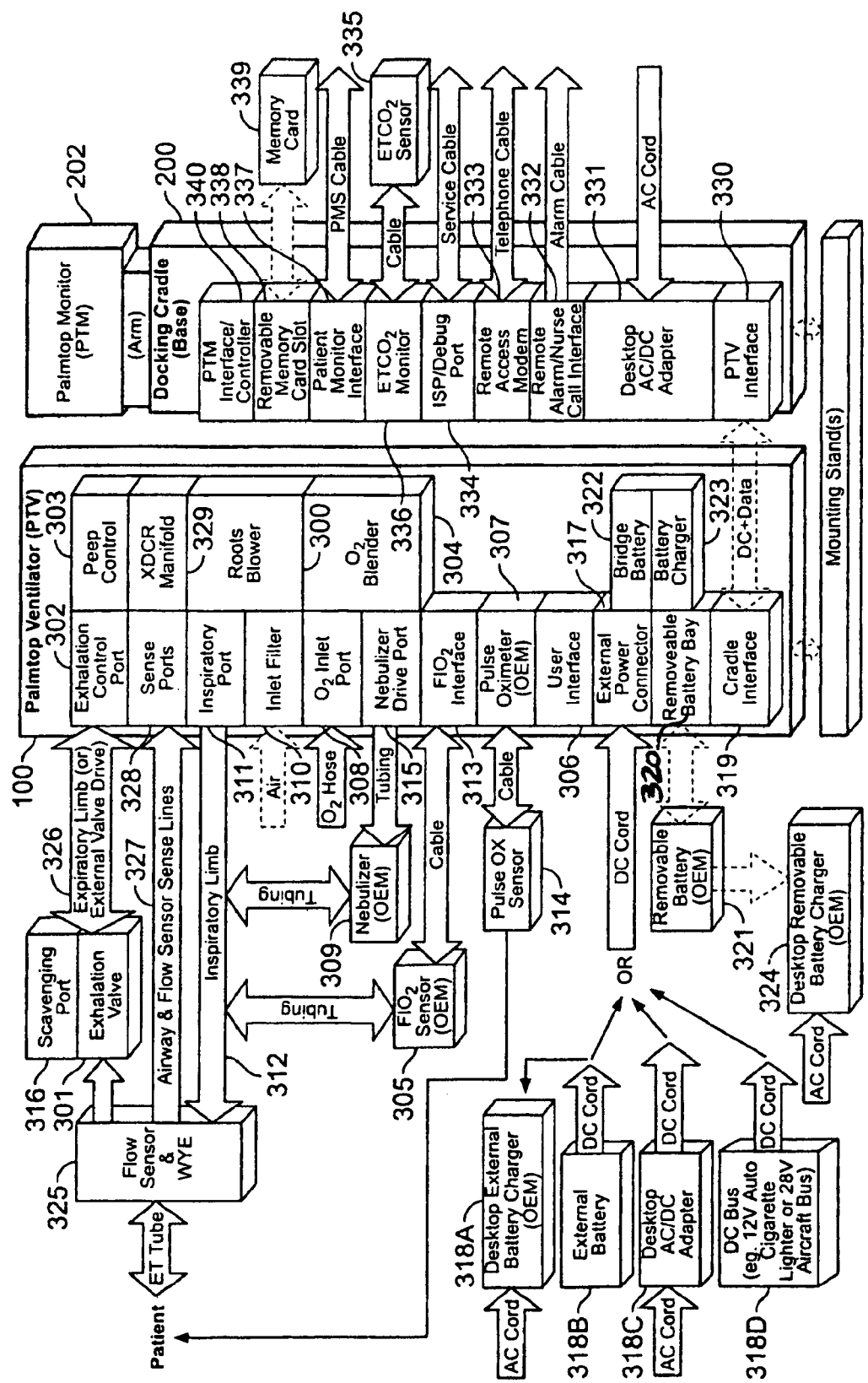
FIG. 3 is a block diagram of a functional architecture for a portable ventilator system in accordance with one or more embodiments of the invention.

FIG. 3 is a block diagram of a ventilator system functional architecture, in accordance with one or more embodiments of the invention. The ventilator pneumatics may be based on a ROOTS-type blower 300 that draws room air through inlet filter 310 and delivers pressurized gas through inspiratory port 311 to the patient. The pneumatic system may support both single limb and dual limb patient circuits, allowing exhalation valve 301 to be implemented either externally or internally with respect to ventilator enclosure 100. Exhalation control port 302 and PEEP (positive end-expiratory pressure) control 303 generate a pilot pressure that closes exhalation valve 301 during inspiration and opens it against a software controlled PEEP pilot pressure during exhalation. Scavenging port 316 may be used to recycle or recirculate the compressed air that is not used by the patient during exhalation.

The ventilator 100 may deliver blended gas using an optional internal $O_2$ blender 304. The blended gas delivery in inspiratory limb 312 may be monitored via an external $FIO_2$ (fraction of inspired oxygen) sensor 305 coupled to $FIO_2$ interface 313, and displayed on user interface 306. Similarly, the patient's blood $O_2$ level may also be monitored via an external pulse oxygen sensor 314 coupled to optional internal pulse oximeter 307, and displayed on user interface 306. When high-pressure oxygen is supplied to $O_2$ inlet port 308, the ventilator 100 may drive an external nebulizer 309 via nebulizer drive port 315 for the delivery of aerosolized drugs to the patient while, at the same time, compensating for the added gas delivery.

One or more embodiments may use a wye ("Y") junction 325 to couple inspiratory limb 312 and expiratory limb 326 to the main ventilator tube to the patient. Airway and flow sensor lines 327 from wye junction 325 enter ventilator enclosure 100 via sense ports 328. Transducer (XDCR) manifold 329 converts the airway and flow values from sense ports 328 into electrical sense signals for use in the ventilator control loop.

In one or more embodiments, the portable ventilator (100) may operate from externally supplied DC power received through external power connector 317 (e.g., from external battery charger 318A, external battery 318B, AC/DC adapter 318C, DC bus 318D, etc.). A cradle interface 319 may allow external power to be supplied to the ventilator without using a cable plug-in. For example, the ventilator enclosure 100 may be dropped into docking cradle 200, where contacts in both devices automatically engage to provide a power path and/or data path. Also, removable battery 321 may be seated in removable battery bay 320 for use of the ventilator as a portable, stand-alone device. The ventilator may be configured with an internal bridge battery (322) to provide continuous power to the ventilator during a swap of removable batteries (321). Battery charger 323 may be used to charge removable battery 321 and/or bridge battery 322 when an external power source is connected to the ventilator enclosure 100. An external removable battery charger (324) may be used to charge extra batteries.

In the embodiment shown in FIG. 3, docking cradle 200 includes a ventilator interface 330 that mates with cradle interface block 319 of ventilator 100 to transfer power and provide electrical connections with interface electronics internal to cradle 200. Optional internal AC/DC adapter 331 within cradle 200 may provide a source of DC power to ventilator 100 via interface blocks 319 and 330, as well as to the circuitry within cradle 200 and monitor 202. Cradle 200 may additionally or alternatively have a DC connector that receives DC power from an external source (e.g., sources 318A 318D).

Cradle 200 may be used to expand the ventilator's interface capabilities to include, for example: a remote alarm/nurse call interface 332 with an output alarm cable; a remote access modem 333; an ISP/debug port 334 (service and maintenance port); an $ETCO_2$ (end tidal carbon dioxide) monitor 336 coupled to an external $ETCO_2$ sensor 335; a patient monitor interface 337 supporting patient monitor systems (such as HP Valuelink and SpaceLabs Flexport); a removable memory card slot 338 for supporting removable memory card 339; and a monitor interface/controller 340. The removable memory card 339 may be used to ease movement of information between the ventilator and a personal computer for data review and printing.

Monitor 202, coupled to arm 201B of cradle 200 is an optional display unit capable of, for example, depicting waveforms, loops, and trend data continuously.

D. Ventilator Electronic Architecture

In one or more embodiments, the portable ventilator electronic architecture may be divided into three major subsystems: a ventilator core subsystem, a user interface subsystem, and a power subsystem. Each subsystem may include one or more software programmable microcontrollers distributed through the subassemblies along with a variety of digital, analog and power circuitry. Other embodiments may divide the electronic architecture along different lines, or not divide the architecture at all.

Figure 4:
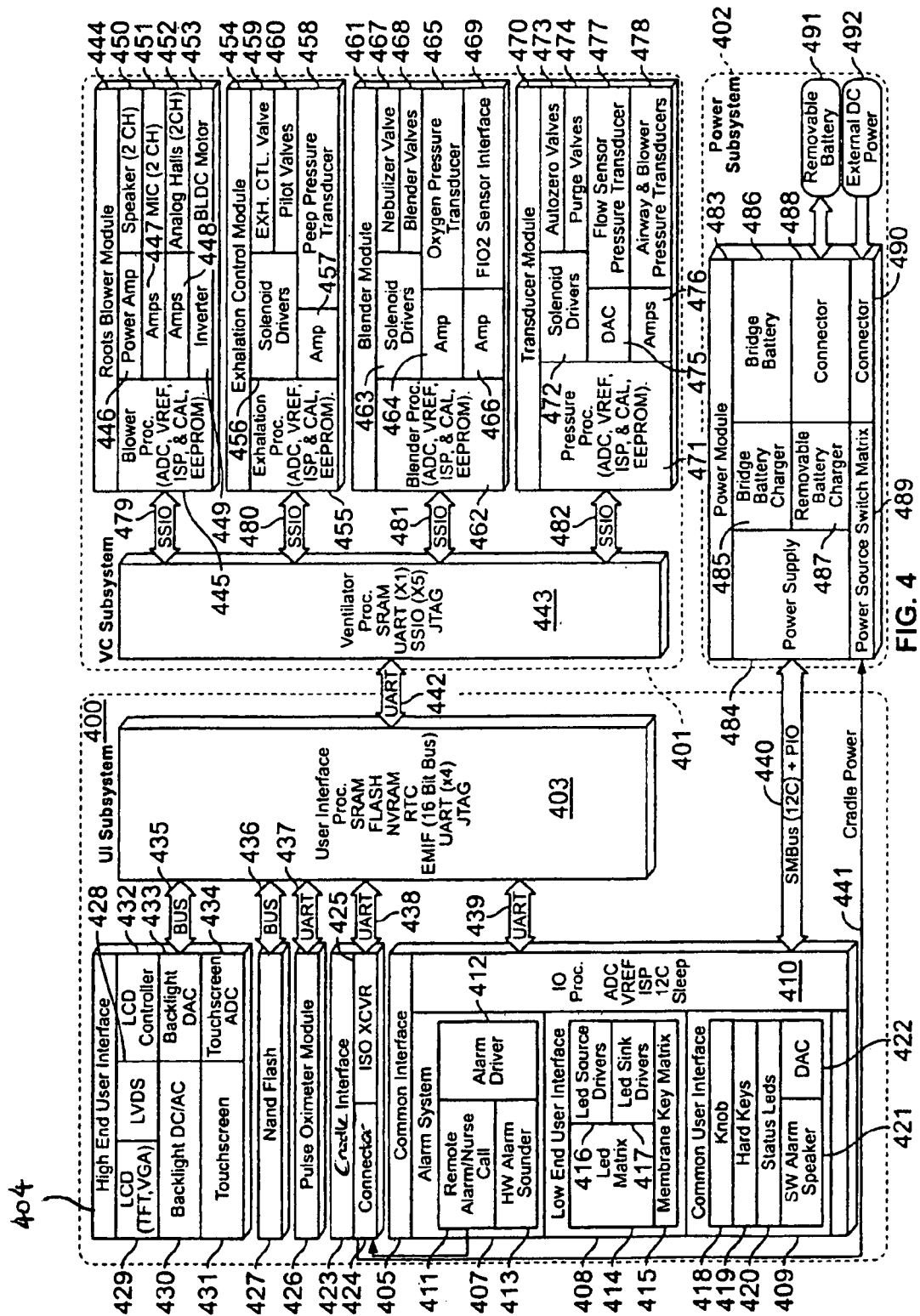
FIG. 4 is a block diagram of an electronic architecture for a portable ventilator system in accordance with one or more embodiments of the invention.

FIG. 4 illustrates one embodiment of the ventilator electronic architecture having a ventilator core (VC subsystem) 401, a user interface (UI subsystem 400 and a power subsystem 402. Each subsystem is described in more detail below.

1. Ventilator Core Subsystem

In the embodiment of FIG. 4, VC subsystem 401 includes electronics for implementing the core gas delivery functions of the portable ventilator. A software program running on the ventilator processor 443 may control the overall ventilator core functionality by commanding and monitoring microcontrollers located within each functional subassembly or module. Each of these microcontrollers may run software programs dedicated to a specific task or tasks of the respective subassembly. In other embodiments, a single processor may be used to execute the tasks of multiple subassemblies. In the illustrated embodiment, VC subsystem 401 includes ventilator processor 443 in communication with respective processors within ROOTS-type blower module 444, exhalation control module 454, blender module 461, and transducer module 470. (In an alternate embodiment, two or more of modules 444, 454, 461 and 470 may be served by a single module processor.)

In ROOTS-type blower module 444, blower processor 445 may control the blower speed through software commutation of a brushless DC motor (BLDC 453) attached to the impellers of a ROOTS-type blower. Inverter 449 may be used to convert the logic level commutation signals from blower processor 445 into high-power AC current to drive BLDC motor 453. Multiple magnetic sensors (e.g., analog Hall sensors 452) within BLDC motor 453 transmit sense signals to blower processor 445 to determine rotor position and speed. An ADC (analog-to-digital converter) circuit may be provided internal to or external to the blower processor IC for the purpose of sampling and converting sense signals, such as those from Hall sensors 452, into digital values for blower processor 445.

Microphones 451 at the ROOTS-type blower intake and outlet ports may be used to monitor the audible noise of the ROOTS-type blower apparatus. The microphone signals are also sampled by the ADC circuit before being processed within blower processor 445. Amplifier circuits 447 and 448 may be used to amplify and filter the microphone and motor sense signals, respectively, prior to the ADC circuit. To reduce the system noise level, blower processor 445 may generate "anti-noise" signals to cancel the blower noise. The anti-noise channels (e.g., one each for the noise at the intake and outlet ports of the blower) may be amplified via power amplifiers 446 that in turn drive a pair of speakers 450 located within the blower ductwork.

The blower processor 445 may include (either on-chip or off-chip) data SRAM, program FLASH memory, and calibration EEPROM. The FLASH and EEPROM memory may be in-system programmable to facilitate manufacturing, service and field software updates. Blower processor 445 may communicate with ventilator control processor 443 via a high-speed synchronous serial port (SSIO 479).

Blower processor 445 may provide a mechanism for calibrating the electronics of blower module 444, and for storing the calibration data within its EEPROM. Blower processor 445 may provide the additional ability to monitor the health of the electronics of blower module 444 and generate self-test feedback to ventilator processor 443 (or a separate test apparatus).

Within exhalation control module 454, exhalation processor 455 may control multiple solenoid valves that generate and pass pilot pressure to the exhalation valve balloon diaphragm. Solenoid valve drivers 456 translate the logic level control signals generated by exhalation processor 455 into high-power DC current to actuate exhalation control valve 459 and PEEP pilot valves 460. Exhalation processor 455 monitors PEEP pressure transducer 458 to enable closed loop control of PEEP pilot valves 460. The analog signals from transducer 458 maybe amplified and filtered by amplifier 457 prior to being A/D converted and sampled by the ADC circuit for exhalation processor 455.

As with blower processor 445, exhalation processor 455 may include (either on-chip or off-chip) data SRAM, program FLASH memory, and calibration EEPROM. The FLASH and EEPROM memory may be in-system programmable to facilitate manufacturing, service and field software updates. Exhalation processor 455 may communicate with ventilator control processor 443 via a high-speed synchronous serial port (SSIO 480).

Exhalation processor 455 may provide a mechanism for calibrating the electronics of exhalation control module 454, and for storing the calibration data within its EEPROM. Exhalation processor 455 may provide the additional ability to monitor the health of the electronics of exhalation control module 454 and generate self-test feedback to ventilator processor 443 (or a separate test apparatus).

Within blender module 461, blender processor 462 controls the flow of oxygen in the system, controls the optional nebulizer drive function, and monitors the external $FIO_2$ sensor via FIO2 sensor interface 469. Solenoid valve drivers 463 translate the logic level control signals generated by blender processor 462 into high-power DC current to actuate blender valves 468 and nebulizer valve 467. Blender processor 462 monitors oxygen pressure transducer 465 to enable closed loop control of blender valves 468. The analog signals from transducer 465 and interface 469 maybe amplified and filtered by amplifier 464 and 466, respectively, prior to being A/D converted and sampled by the ADC circuit for blender processor 462.

As with the blower and exhalation processors, blender processor 462 may include (either on-chip or off-chip) data SRAM, program FLASH memory, and calibration EEPROM. The FLASH and EEPROM memory may be in-system programmable to facilitate manufacturing, service and field software updates. Blender processor 462 may communicate with ventilator control processor 443 via a high-speed synchronous serial port (SSIO 481).

Blender processor 462 may provide a mechanism for calibrating the electronics of blender module 461, and for storing the calibration data within its EEPROM. Blender processor 462 may provide the additional ability to monitor the health of the electronics of blender module 461 and generate self-test feedback to ventilator processor 443 (or a separate test apparatus).

Within transducer module 470, pressure processor 471 measures critical system pressures and manages periodic auto zero and sense line purge functions. Solenoid valve drivers 472 translate the logic level control signals generated by pressure processor 471 into high-power DC current to actuate autozero valves 473 and purge valves 474. Pressure processor 471 monitors flow sensor pressure transducer 477 and airway and blower pressure transducers 478.

Amplifiers 476 amplify and filter the sense signal outputs of transducers 477 and 478 before those sense signals are sampled and processed by pressure processor 471. In one embodiment, two parallel amplifiers may be dedicated to flow sensor pressure transducer 477. One amplifier may provide a high-gain, narrow-range, offset-compensated flow trigger channel. The offset compensation is provided using a software-controlled DAC (digital-to-analog converter) circuit 475. A second channel may provide a lower gain amplifier to cover the full bi-directional dynamic range of flow into and out of the patient. Amplifiers 476 also provide amplified airway gauge pressure and blower differential pressure signals.

As with the other module processors, pressure processor 471 may include (either on-chip or off-chip) data SRAM, program FLASH memory, and calibration EEPROM. The FLASH and EEPROM memory may be in-system programmable to facilitate manufacturing, service and field software updates. Pressure processor 471 may communicate with ventilator control processor 443 via a high-speed synchronous serial port (SSIO 482).

Pressure processor 471 may provide a mechanism for calibrating the electronics of transducer module 470, and for storing the calibration data within its EEPROM. Pressure processor 471 may provide the additional ability to monitor the health of the electronics of transducer module 470 and generate self-test feedback to ventilator processor 443 (or a separate test apparatus).

2. User Interface Subsystem

User interface (UI) subsystem 400 includes the electronics to create the interface to the device user and external peripherals. In one or more embodiments, UI subsystem 400 may provide the user with information, such as audible and visual feedback regarding the patient status, machine status, alarm conditions, and control settings. UI subsystem 400 monitors the user inputs (e.g., knob and buttons) and communicates settings to ventilator processor 443 of ventilator core subsystem 401 via a serial channel (e.g., UART 442). Also, in one or more embodiments, UI subsystem 400 monitors and controls power subsystem 402, maintains device configuration and control settings in non-volatile memory, acts as a recorder of events and user actions, and communicates with any accessory devices (e.g., docking cradle 200, internal pulse oximeter 307, etc.).

Within UI subsystem 400, user interface processor 403 executes a software program that controls the overall user interface functionality. The program FLASH memory associated with user interface processor 403 may be in-system programmable to facilitate manufacturing, service and field software updates. In one or more embodiments, certain tasks, such as refreshing displays and scanning keys, may be delegated to a programmable microcontroller and/or dedicated hardware controllers located within user interface subassemblies. The functionality of possible UI subassemblies is described below.

The ventilator user interface may be implemented with a variety of display and input/output mechanisms. For example, one user interface embodiment (labeled as high end user interface 404) utilizes a color LCD (liquid crystal display: e.g., TFT or VGA) graphics panel 429 and an analog touch screen overlay 431 to provide a flexible user interface with high information content. Interface 404 is coupled to UI processor 403 via bus 435. LCD controller 432 may perform the time-intensive task of refreshing LCD 429 from a RAM image buffer (on-chip or off-chip) via a high-speed LVDS (low voltage differential signaling) interface 428. The UI software may restrict updates of the image buffer to time periods during which the display content actually changes.

Backlight inverter 430 powers the LCD backlight. Screen brightness may be controlled by the UI software using backlight DAC 433. The touch screen ADC/controller 434 performs scans of the touch screen overlay 431, and provides the UI software with an interrupt and data during periods of touch activity.

Another user interface embodiment alternatively or additionally may use a low end user interface 408 including, for example, a combination of dot matrix, seven-segment and/or discrete LEDs (represented as LED matrix 414) and a membrane key matrix 415. LED matrix 414 is driven by LED source drivers 416 and LED sink drivers 417. IO (input/output) processor 410 may perform the task of refreshing the LED matrix 414 from a RAM image buffer. The UI software may update the image buffer when its content changes. IO processor 410 also performs the task of scanning key matrix 415 and providing the UI software with an interrupt and data during periods of key activity.

Both user interface options (high-end interface 404 and low end interface 408) may use a common user interface 409 that includes a knob (e.g., a rotary switch) 418, one or more hard keys 419 for dedicated functions, status LEDs 420 and an audible software alarm speaker 421. IO processor 410 may track knob 418 and hard keys 419, and provide the UI software with an interrupt and data during periods of knob and/or hard key activity. IO processor 410 may also synthesize software alarms and control status LEDs 420 based on commands from the UI software with the aid of digital-to-analog (DAC) 422.

An optional internal pulse oximeter module 426, whose external sensor is placed on the patient's finger, provides monitor data such as pulse rate and oxygen saturation level to user interface processor 403. User interface processor communicates with module 426 over a serial interface such as UART 437.

Cradle interface 423 includes a connector 424, for electrically engaging a mating connector on the docking cradle, and a transceiver (e.g., ISO XCVR 425) to allow communication (e.g., via a serial UART interface 438) between the ventilator and the docking cradle electronics at moderate data rates. DC power may also be transferred through this interface (see cradle power line 441 from connector 424 to power module 483) from the docking cradle to the ventilator. The ventilator may also provide a remote alarm/nurse call signal through cradle interface 423 to the outside world.

A non-volatile memory circuit (e.g., NAND FLASH 427) may be included in UI subsystem 400 for long term logging of ventilator events and control settings changes (like a "black box" recorder). User interface processor 403 may write directly into non-volatile memory 427 via a parallel bus (436), for example.

IO processor 410 may also act as the supervisor for power subsystem 402. For example, IO processor 410 may monitor all power inputs and power supply outputs, manage the selection of the active input power source (via power source switch matrix 489), and control the two internal battery chargers (485 and 487). Additionally, IO processor 410 may monitor the state of the "ON/OFF" and "ALARM SILENCE/RESET" hard keys and drive the "ON/OFF", "VENT INOP", "ALARM SILENCE", "EXTERNAL POWER", "BATTERY STATUS", and "CHARGE STATUS" LEDs on common interface 409.

IO processor 410 may act as the device watchdog. For example, in one embodiment, each subassembly must periodically report good health back to IO processor 410. In turn, IO processor 410 must periodically report good health to alarm driver 412 of alarm system 407. If alarm driver 412 fails to receive good health updates, then the audible hardware alarm (INOP) 413 and remote alarm/nurse call outputs (411) are activated. Alarm driver 412 may also trigger a device reset to attempt to restart the life support function. The common user interface 409, low end user interface 408 and alarm system 407 collectively comprise common interface 405 which communicates with UI interface 403 through serial interface UART 439.

3. Power Subsystem

Power module 483 provides power to the ventilator and is connected thereto by bus 440. The ventilator may be powered from either an external DC source (e.g., external power source 492 or cradle interface 423) via connector 490, or an internal source (e.g., removable battery 491 or bridge battery 486). Bridge battery 486 may be sized to provide seamless operation of the ventilator while removable battery 491 is swapped from connector 488. Two independent internal chargers (485 and 487) may be included for purposes of maintaining charge on removable battery 491 and bridge battery 486. Power supply 484 may include several switching and/or linear power supplies to provide the DC voltages used throughout the ventilator system.

E. Docking Cradle Electronic Architecture

Figure 5:
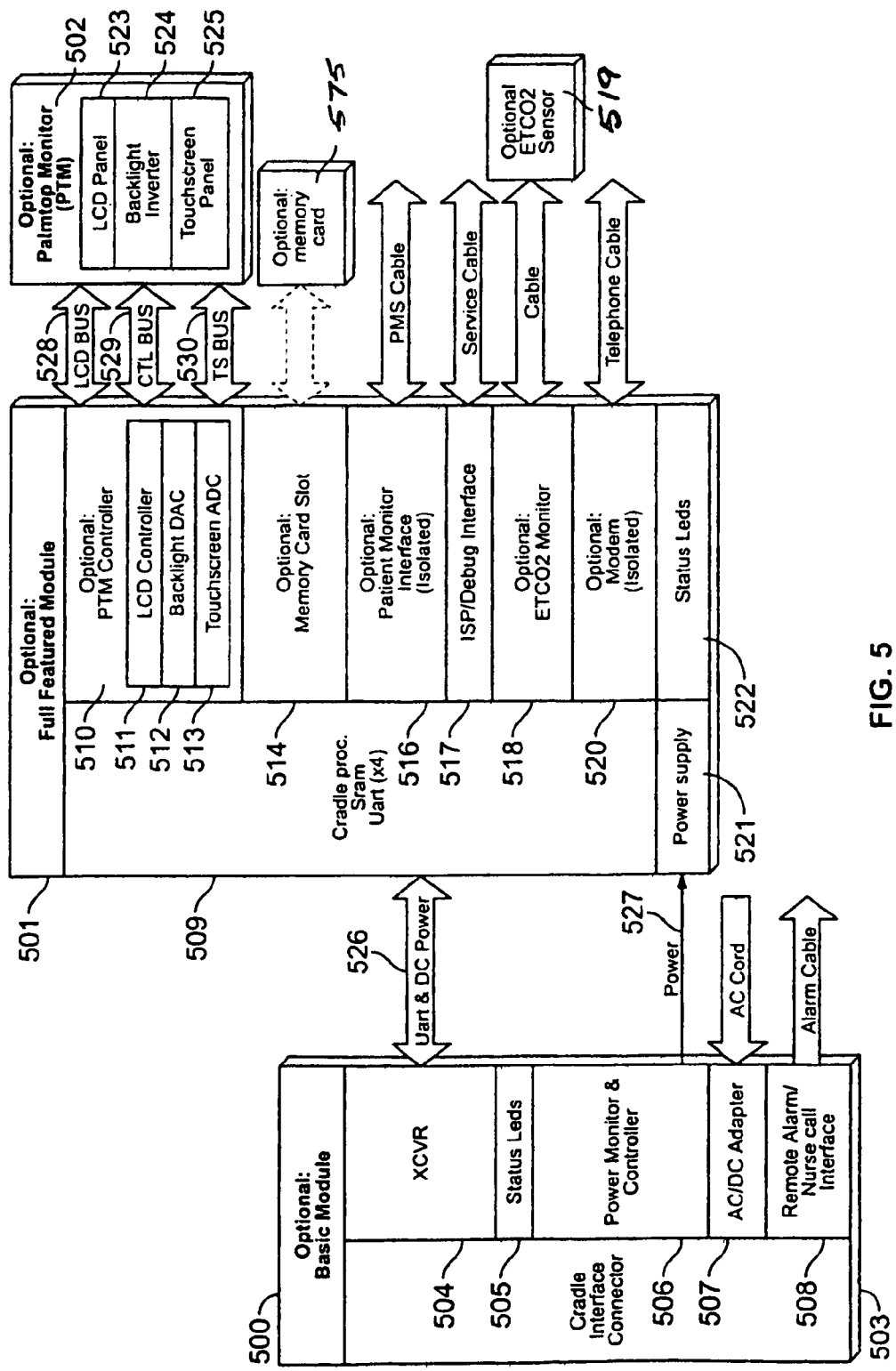
FIG. 5 is a block diagram of an electronic architecture for a docking cradle in accordance with one or more embodiments of the invention.

FIG. 5 is a block diagram of the electrical architecture for one embodiment of the docking cradle 200. As shown, the docking cradle is divided into a basic module 500 and a full-featured module 501. Basic module 500 provides basic power and status indicators, as well as an alarm cable output. Full-featured module 501 provides additional processing power, as well as further connection interfaces, monitoring capability and support for an additional display monitor. The division of features is shown to highlight the range of capabilities that may, but need not be, implemented within the docking cradle. The illustrated features are not intended to be exhaustive, nor do they represent required features. Different embodiments of the docking cradle may include different combinations and different numbers of features without departing from the scope of the invention.

In the illustrated embodiment, basic module 500 includes cradle interface connector 503, which mates electrically with cradle interface connector 424 of the ventilator. DC power is supplied to the ventilator through power line 527 via AC/DC adapter 507, which may receive AC power from an external source (e.g., from a cable attached to a wall outlet). AC/DC adapter 507 may also provide DC power to full-featured module 501 via power monitor and controller block 506. The remote alarm/nurse call outputs from the ventilator (see block 411, FIG. 4) are made available for attachment of an external alarm cable (e.g., to plug into a wall jack or device in a hospital room) through remote alarm/nurse call interface 508. If full-featured module 501 is present, then a transceiver (XCVR) circuit 504 may be implemented to facilitate communication with the ventilator over the cradle interface connector 503. Transceiver circuit 504 may communicate with cradle processor 509 over a serial interface, such as a UART interface 526. Hardware driven status LEDs 505 in basic module 500 provide basic device status, such as the active presence and/or health of AC/DC adapter 507 and of the connection with the ventilator.

Full-featured module 501 may be implemented to further expand the interface capabilities of the docking cradle to include, for example, the following options: support for an additional display monitor (502), memory expansion by the addition of one or more memory cards 575 (e.g., compact FLASH memory cards) in memory card slot(s) 514, an additional patient monitoring interface 516, an internal ETCO2 monitor 518 (coupled to an external ETCO2 sensor 519), and a modem 520 (e.g., for remote access via telephone).

A software program executed by cradle processor 509 controls the optional features of full-featured module 501. Cradle processor 509 may include (either on-chip or off-chip) data SRAM memory, program FLASH memory, and battery-backed SRAM. The FLASH memory may be in-system programmable, via the ISP/debug interface (service port) 517, to facilitate manufacturing, service and field software updates.

In full-featured module 501, power supply 521 may be provided to perform DC-DC conversion to generate all of the supply voltages needed by the full-featured module circuitry. Software driven status LEDs 522 may be included to show the on/off state and health of the module electronics.

To provide support for an additional display monitor 502, full-featured module 501 may be equipped with monitor PTM controller 510. Monitor controller 510 includes an LCD controller 511 (assuming the monitor is an LCD monitor), backlight DAC 512 and touch screen ADC 513. LCD controller 511 supplies data and control signals to LCD panel 523 over LCD bus 528 and control (CTL) bus 529, respectively; backlight DAC drives backlight inverter circuit 524; and touch screen ADC 513 controls touch screen panel 525, as well as receiving touch screen data, over TS bus 530. In other embodiments, additional or different features may be embodied within full-featured module 501.

F. General Software Architecture for Ventilator System

In one or more embodiments, the ventilator and docking cradle contain embedded software (and/or firmware) that control the respective hardware and determine the operating characteristics of the system. This software may be split between multiple processors distributed throughout the system on various subassemblies. FIG. 6 is a block diagram illustrating the context of the general software architecture of a ventilator system, in accordance with one or more embodiments of the invention.

Figure 6A:
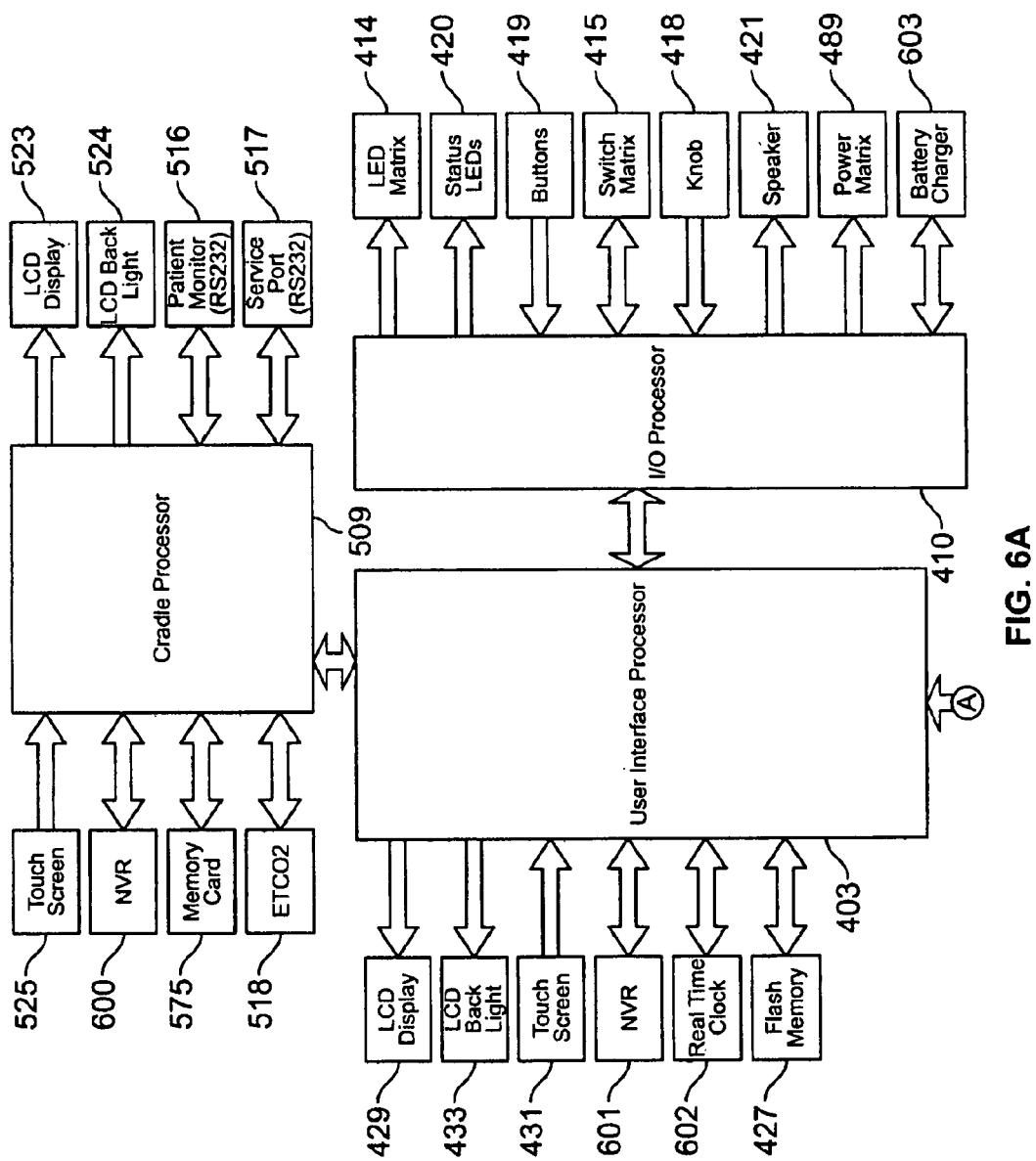
FIGS. 6A and 6B are block diagrams illustrating the general context of a software architecture for a portable ventilator system in accordance with one or more embodiments of the invention.
Figure 6B:
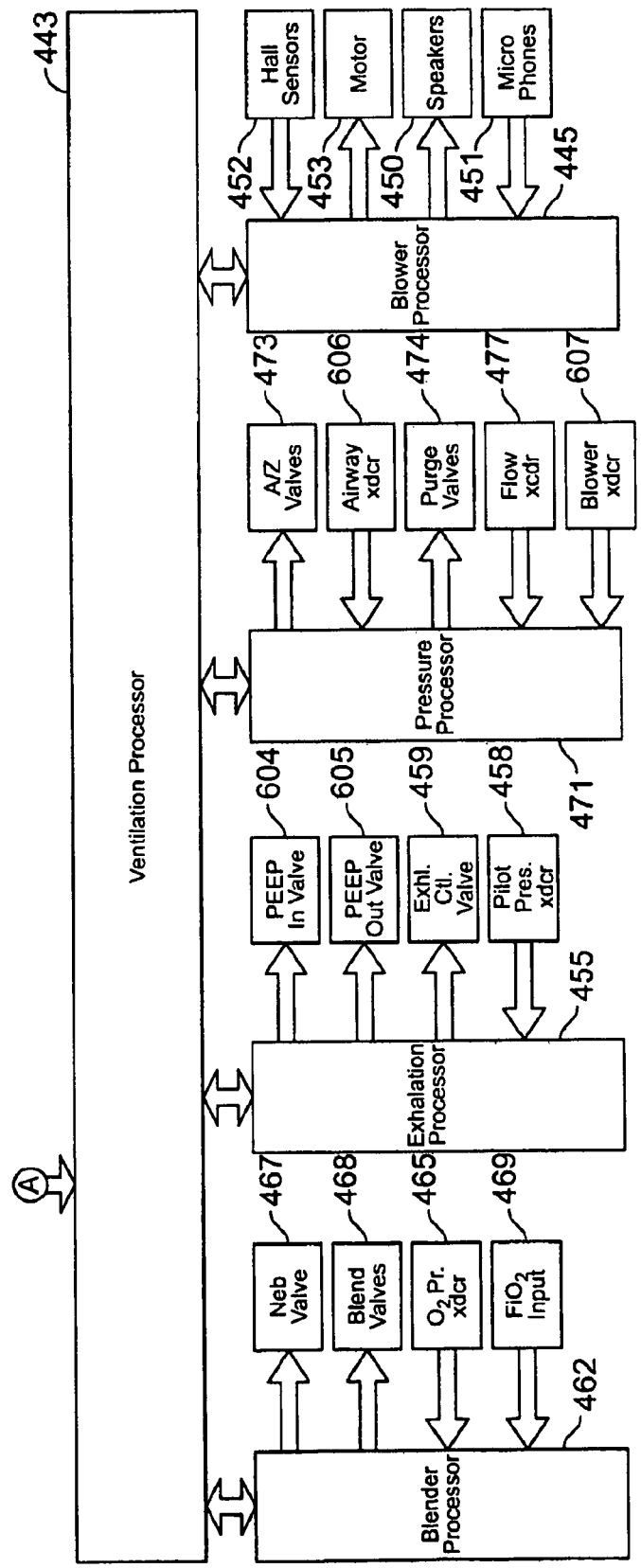

FIGS. 6A and 6B, the software for the ventilator system is distributed among the following processors: user interface processor 403, 10 processor 410, ventilation processor 443, blender processor 462, exhalation processor 455, pressure processor 471, blower processor 445, and cradle processor 509. Various functions of the software executed by those respective processors are described below. The functions described are presented for illustrative purposes only and should not be considered as either the only nor as required functions for all embodiments. For ease of discussion, the software running on each processor will be referred to with reference to the name of the processor (i.e., the software executing on the user interface processor is referred to as the user interface software, the software running on the blender processor is referred to as the blender software, etc.).

The user interface software (executing on user interface processor 403) may be configured to communicate with IO processor 410 (via bus 439, as shown in FIG. 4) and cradle processor 509, as well as to send ventilation control data (e.g., settings and alarm limits) to ventilation processor 443. The user interface software may store application code received from cradle processor 509 into FLASH memory 427, and update application code for IO processor 410, ventilation processor 443, blender processor 462, exhalation processor 455, pressure processor 471 and blower processor 445. The user interface software may also store trend data, vent settings and user configuration data in non-volatile RAM (NVR) 601, and, with the aid of real-time clock 602, may log all events, such as control changes, alarms and failures, in the "black box" portion of FLASH memory 427. The user interface software drives the LCD user interface (LCD 429, touch panel 431 and backlight 433), for example, to display alarm data and/or monitored data received from ventilation processor 443.

The IO software (executing on IO processor 410) may be configured to communicate with user interface processor 403 to provide an intelligent controller for attached peripheral circuits and devices. For example, the IO software may provide low level drivers for status LEDs 420, common buttons (or keys) 419, knob 418 and speaker 421. In addition, the IO software may be configured to refresh LED matrix 414, scan key matrix 415, and control the power switch matrix 489 and battery charger(s) 603 (485, 487).

The ventilation software (executing on ventilation processor 443) may be configured to control primary functions, such as the generation of breaths, implementation of the pressure servo, and sequencing of maneuvers (e.g., nebulizer activation, I-hold (inhalation hold), E-hold (exhalation hold), etc.). The ventilation software may also be configured to compute monitored parameters, compare monitored values to alarm limits, and schedule auto zero functions for pressure processor 471.

The blender software (executing on blender processor 462) may be configured to control nebulizer valve 467 and implement the blending servo to control blend valves 468. The blender software may also monitor and calibrate the $O_2$ transducer 465, manage calibration of the $FIO_2$ sensor 469 and forward $FiO_2$ data to ventilation processor 443.

The exhalation software (executing on exhalation processor 455) may be configured to implement the PEEP servo for control of PEEP in-valve 604 and PEEP out-valve 605 based on the input from pilot pressure transducer 458. The exhalation software may also control exhalation valve 459 and manage calibration of the pilot pressure transducer and the PEEP servo.

The pressure software (executing on pressure processor 471) may be configured to provide calibrated trigger pressure readings and flow sensor pressure readings from flow transducer 477, calibrated blower differential pressure readings from blower transducer 607 and calibrated airway pressure readings from airway transducer 606 to ventilation processor 443. The pressure software may also implement auto zero and purge functions with auto zero valves 473 and purge valves 474.

The blower software (executing on blower processor 445) may be configured to implement the speed servo and commutate the blower motor 453. To facilitate implementation of the speed servo and commutation of motor 453, the blower software may also calibrate the motor position sensors (e.g., Hall sensors 452) and compute rotor position and speed from the outputs of the motor position sensors 452. The blower software may also implement active braking of motor 453 and active sound canceling (e.g., using inputs from microphones 451 and generating anti-noise outputs via speakers 450.

The cradle software (executing on cradle processor 509) may be configured to communicate with user interface processor 403, and to display ventilation data (e.g., waves, loops, data, summary and trends) on LCD display 523. The cradle software may also be configured to store trend data in non-volatile RAM (NVR) 600 and print images on memory card 575. The cradle software may collect ETCO2 data from ETCO2 monitor 518 and transmit that data to the ventilator via user interface processor 403. Additionally, patient data and alarms may be forwarded to other patient monitor systems (e.g., via port 516).

II. Ventilator Pneumatics in One Embodiment

Figure 7:
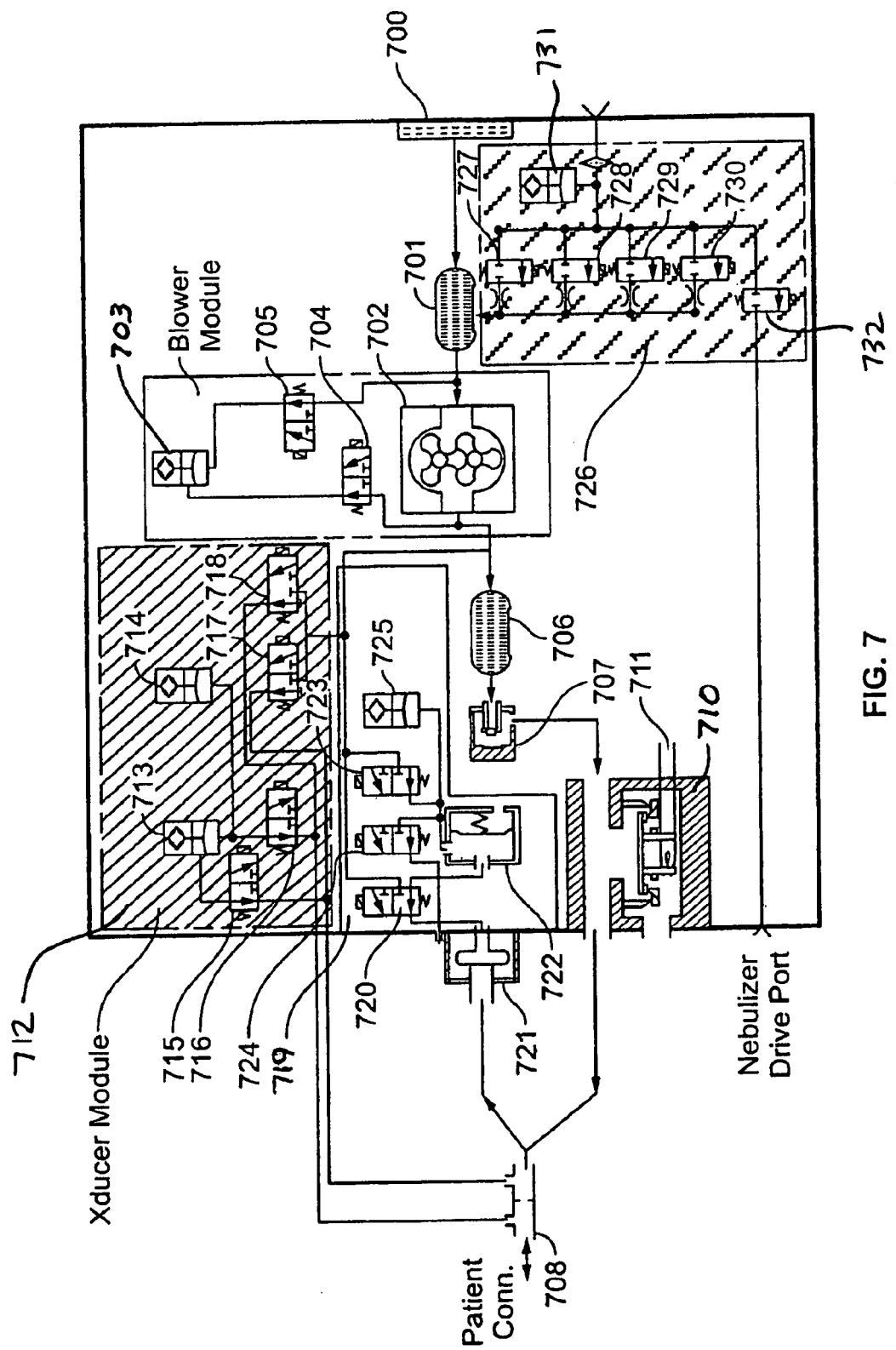
FIG. 7 is a pneumatic diagram of a portable ventilator in accordance with one or more embodiments of the invention.

The ventilator pneumatics comprise several electromechanical subassemblies in one or more embodiments of the invention. Ventilating functionality is provided by computer control of the pneumatic functions of those electromechanical subassemblies. FIG. 7 is a pneumatic diagram of one embodiment if the ventilator.

In the system of FIG. 7, room air is drawn in through inlet filter 700, after which the air travels through a combination accumulator/silencer chamber 701 where the air may be mixed with oxygen. Chamber 701 also serves to absorb noise produced on the inlet side of ROOTS-type blower 702. ROOTS-type blower 702, driven for example by a brushless DC motor, is a rotary positive displacement machine that adds energy to the gas mixture and supplies gas to the patient at the desired flow and pressure.

In one embodiment, ROOTS-type blower 702 may be characterized according to speed, flow, differential pressure and the associated flow data stored in electronic memory for use by ventilator processor 443 in alternately accelerating and decelerating the blower to effect inspiration and permit exhalation. Analog position sensors (e.g., Hall sensors) measure the rotor position within the motor, from which blower processor 445 may compute the rotational speed of ROOTS-type blower 702. Differential pressure transducer 703 measures pressure across the blower. The ventilator processor 443, working in conjunction with blower processor 445, may adjust the blower speed throughout the inspiratory phase to obtain the desired flow, volume and pressure. Solenoid valves 704 and 705 provide auto-zero capability for the differential pressure transducer 703.

Silencer chamber 706 on the gas outlet side of ROOTS-type blower 702 reduces blower noise. The gas then travels through bias valve 707, set, for example, on or about 5 cmH2O.

Patient flow transducer 708, a fixed orifice differential pressure type transducer, measures the flow to and from the patient. Overpressure relief valve 709 and sub-ambient relief valve 710 are internal and provide mechanical fail-safes to insure patient safety in the event of major ventilator malfunction. MIPINIF lockout coil 711 is included in sub-ambient relief valve 710 to prevent opening of the valve during maximum inspiratory pressure (MIP) procedures.

Pressure transducer module 712 provides the basic pressure measuring capabilities of the system. For example, three Piezo-resistive pressure transducers form flow sensor differential pressure transducer 713 to measure differential pressure across patient flow transducer 708 and an airway gauge pressure transducer 714 to gauge the pressure at the patient airway. Solenoid valves 715 and 716 provide auto-zero capability for flow sensor differential pressure transducer 713, while valves 717 and 718 periodically send dry gas from the blower outlet through the patient flow transducer sense lines as part of a purge cycle.

Exhalation control module 719 allows the patient to exhale in accordance with the desired PEEP. During inspiration, exhalation control solenoid 720 feeds gas pressure from the blower outlet to the balloon diaphragm of exhalation valve 721, which closes the exhalation valve. During exhalation, pilot pressure from pilot pressure accumulator 722 is fed to the balloon, which establishes the PEEP level. The pilot pressure in accumulator 722 is controlled through pulse-width modulation (PWM) of pilot-in solenoid valve 723 and pilot-out solenoid valve 724, using feedback from pilot pressure transducer 725.

Oxygen blending and nebulizer drive are controlled in blender module 726. Pressurized gas is received from an external source, filtered, and fed into the chambers of noise attenuation system 701 under the PWM control of solenoid valves 727, 728, 729 and 730 having associated orifices. Each solenoid valve orifice may be characterized during initial assembly, and the associated flow data may be stored in electronic memory on a PCB within module 726. O₂ pressure transducer 731 measures the valve inlet pressure. Using inlet pressure, the stored orifice characterizations, and PWM, the blender controller can deliver the range of oxygen flow desired. Nebulizer drive solenoid valve 732 and its associated orifice may deliver content, such as aerosolized medication, to the drive port of valves 727 730 during the inspiratory phase. The quantity of content may be, for example, on or about 6 l pm of oxygen flow. System software may adjust the delivery of oxygen and volume to compensate for the added nebulizer flow.

As previously described, variable speed ROOTS-type blower 702 is alternately accelerated and decelerated by ventilator processor 443 as necessary to effect inspiration and expiration. In an alternate embodiment, ROOTS-type blower 702 is maintained by ventilator processor 443 at a relatively constant speed, generating a relatively constant flow of gas at a flow rate and pressure suitable for ventilating the lungs of a patient. A downstream flow control valve is utilized to control the flow of gas to the patient, opening to effect inspiration and closing to permit exhalation. In this alternate embodiment, the unique pressure and flow output of each ROOTS-type blower 702 need not be measured during production and no individualized blower characterization data need be stored for use by the ventilator processor 443.

III. Exhalation Control Servo Embodiment

One or more embodiments of the invention implement an exhalation control servo to generate an actual PEEP pressure from a desired PEEP pressure value. The desired PEEP pressure value is a digital value representative of a PEEP pressure. The actual PEEP pressure is a controlled force per unit area generated from the blower pressure of ROOTS-type blower 702. The exhalation servo comprises electromechanical apparatus for achieving this conversion from the digital domain to the pneumatic domain.

Figure 8:
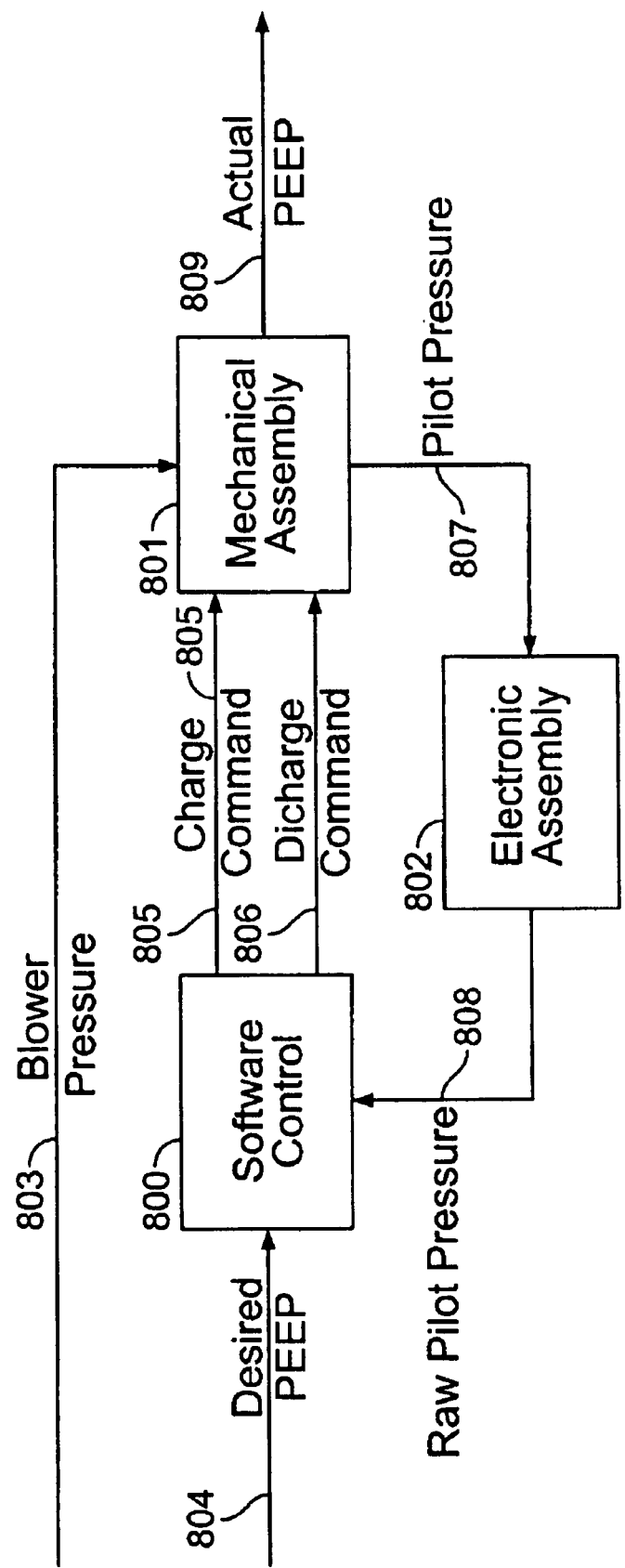
FIG. 8 is a top level block diagram of an exhalation servo control system in accordance with one or more embodiments of the invention.

FIG. 8 is a block diagram showing an exhalation servo loop, in accordance with an embodiment of the invention. The exhalation control servo of FIG. 8 includes a software control block 800, a mechanical assembly 801 and an electrical assembly 802. In operation, software control block 800 receives the digital desired PEEP value 804 (e.g., from ventilator processor 443) and a digital value of the current raw pilot pressure 808, and generates a charge command 805 for increasing the output pressure of the servo loop and a discharge command 806 for reducing the output pressure. Commands 805 and 806 are in electrical form (e.g., digital).

Mechanical assembly 801 receives the charge and discharge commands (805, 806) from software control 800, as well as a physical blower pressure 803, in pneumatic form. Mechanical assembly 801 applies blower pressure 803 in accordance with the charge and discharge commands to generate a pilot pressure feedback value 807 and actual PEEP value 809, both in pneumatic form. Electronic assembly 802 transforms pilot pressure 807 into raw pilot pressure signal 808, in digital form for processing by software control 800.

FIG. 9A is a block diagram of mechanical assembly 801, in accordance with an embodiment of the invention. In mechanical assembly 801, charge command 805 is applied to charge valve 723 to control the amount of blower pressure 803 released into pilot chamber 722. Discharge command 806 is applied to discharge vale 724 to control the release of pressure from pilot chamber 722. In one embodiment, charge command 805 and discharge command 806 are implemented as PWM signals. Pilot chamber 722 accumulates the pressure effects of opening and closing valves 723 and 724. The accumulated pressure is output as pilot pressure 807. Chamber 900 may embody the balloon diaphragm of the exhalation control valve, which asserts the actual PEEP pressure 809.

FIG. 9B is a block diagram of an embodiment of electronic assembly 802. The pilot pressure 807 is converted into pilot pressure sense signal 901 by pressure transducer 714. Preamplifier 902 amplifies pilot pressure sense signal 901 and low-pass filter 903 removes any noise and upper harmonics in the amplified signal. The amplified and filtered sense signal is then sampled by sample-and-hold circuit 904 and subsequently converted into the digital raw pilot pressure value 808 in ADC block 905.

Figure 9C:
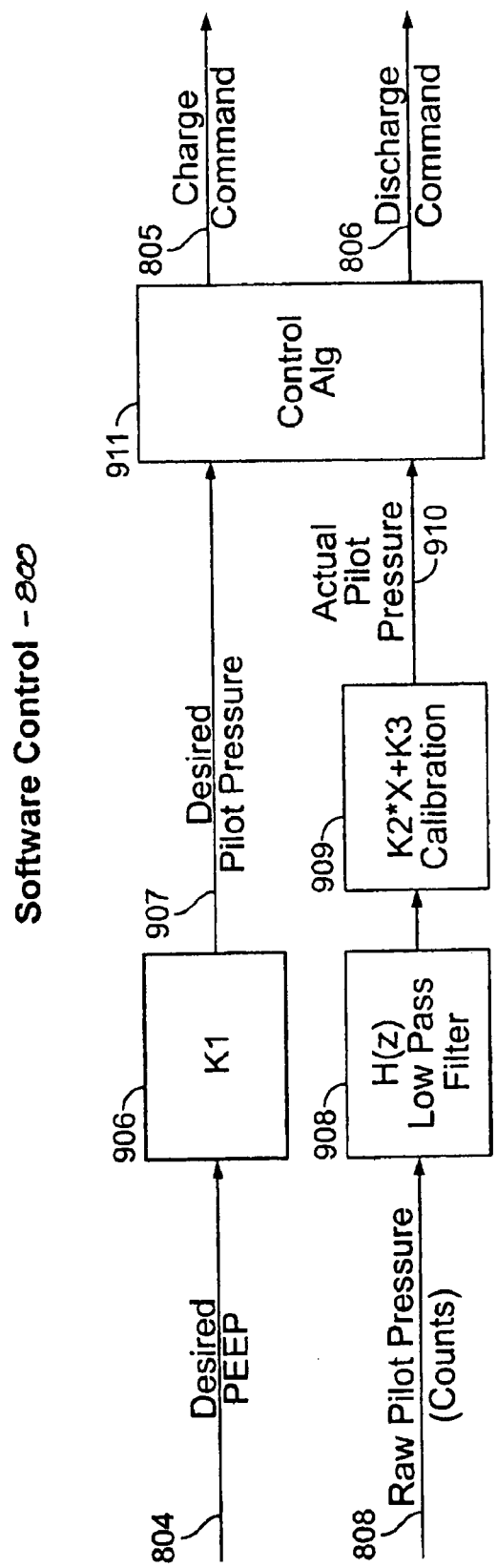
FIG. 9C is a block diagram of a software control portion of an exhalation servo control system in accordance with one or more embodiments of the invention.

FIG. 9C is a block diagram of an embodiment of software control block 800. In block 906, the desired PEEP value 804 is applied to a function to generate desired pilot pressure value 907. The function implemented within block 906 may be a simple table look-up based on known (i.e., calibrated) values of pilot pressure for a given PEEP value. Alternatively, that function may be a mathematical model that approximates the inverse of the relationship between a pilot pressure input into chamber 900 and the PEEP value that results.

Digital low-pass filter 908 receives raw pilot pressure signal 808 and bandlimits that signal to maintain a desired servo loop response. Block 909 implements a mathematical function that approximates the inverse of the characteristics of the transducer in block 714. Any variance in pilot pressure values due to the behavior of the transducer may be corrected by block 909.

The mathematical model for block 909 may be created by calibrating the transducer during production and storing raw and actual pilot pressure values. A mathematical equation may then be constructed to approximately reverse the effects of the transducer by determining coefficients for the equation through the application of least squares curve fitting or similar techniques on the calibration data.

In block 911, the desired pilot pressure 907 and the actual pilot pressure 910 are compared to determine an error value, and that error value is applied to a control algorithm (e.g., a PI or PID algorithm) to generate charge command 805 and discharge command 806. In one embodiment, the binary states of the charge and discharge commands are determined at periodic intervals. If the measured pilot pressure exceeds the desired pilot pressure by a threshold amount, then the discharge command is asserted during that interval, whereas if the measured pilot pressure falls below the desired pilot pressure by more than a threshold amount, the charge command is asserted during that interval. When the measured pilot pressure resides within the threshold range of the desired pilot pressure, neither command is asserted (maintain status quo for current interval).

IV. Embodiment of ROOTS-Type Blower Assembly

The present invention involves the precision speed control of an electric motor that may be used to drive a compressor in a mechanical ventilator. Mechanical ventilators may have various modes of operation, e.g., pressure control and volume control. One common thread amongst most mechanical ventilators is that the desired operating mode is achieved by controlling the gas flow rate produced by the gas compressor. An example of a suitable compressor control system for a blower assembly is further described in U.S. patent application Ser. No. 10/847,693, filed May 18, 2004, the specifications and figures of which are herein incorporated by reference.

In one embodiment, the compressor motor is a brushless DC (BLDC) motor driving a ROOTS-type blower used as a compressor in a portable mechanical ventilator. The flow rate and pressure provided by the compressor are controlled by the speed of the BLDC motor. Unlike in prior art systems where digital Hall effect sensors are used to provide discrete samples of the rotor position and separate speed transducers are used to provide speed feedback of the BLDC motor, embodiments of the present invention may employ analog sensors (e.g., analog Hall effect sensors, anisotropic magneto-resistive (AMR) sensors, etc.) to provide continuous rotor position and speed feedback for closed loop control.

Figure 10:
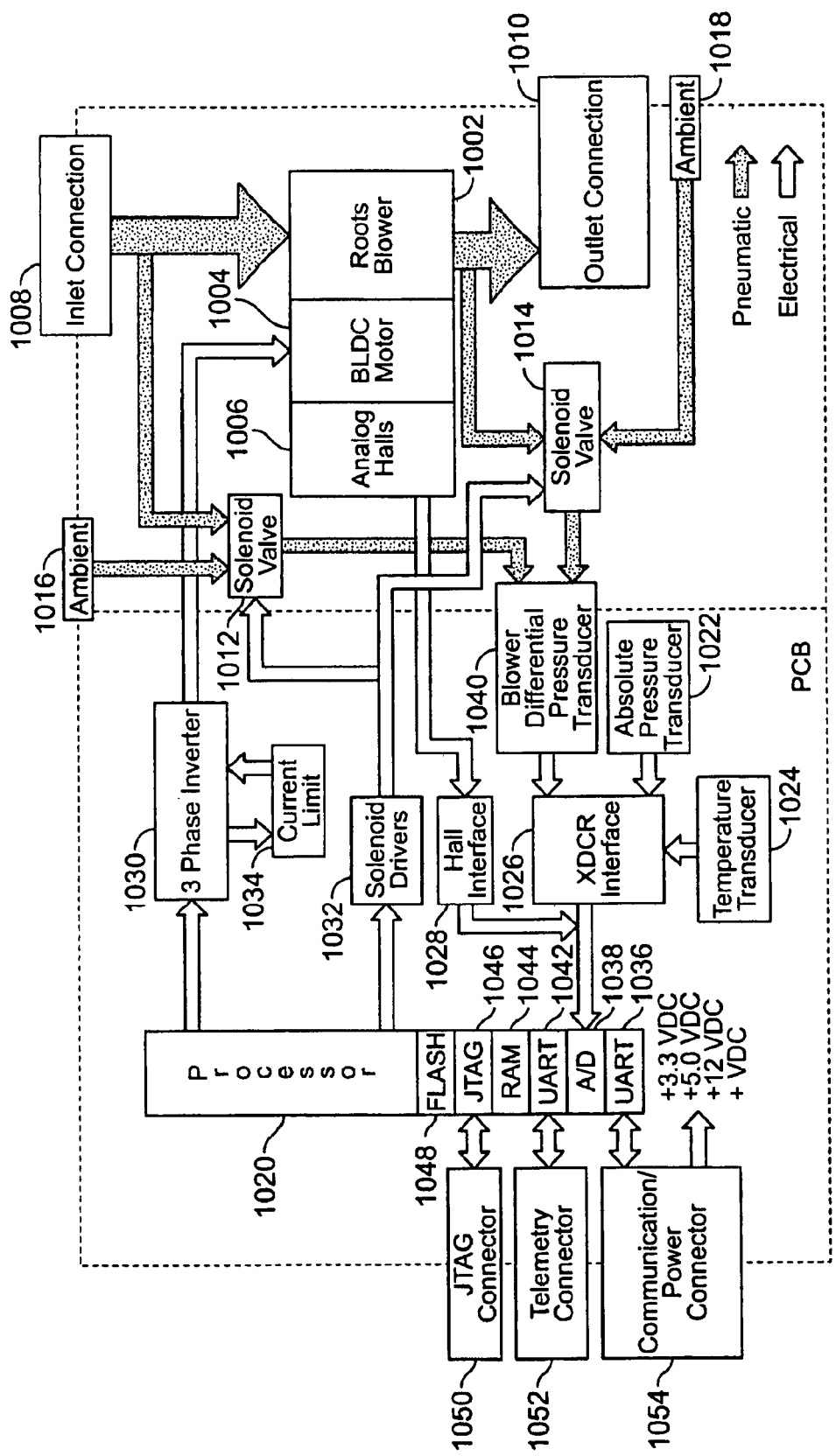
FIG. 10 is a block diagram of a blower assembly in accordance with one or more embodiments of the invention.

FIG. 10 is a block diagram of a motor/compressor system in accordance with an embodiment of the present invention. In this illustration, the motor/compressor system comprises ROOTS-type blower 1002 coupled to BLDC motor 1004. Gas (i.e., air) enters Roots blower 1002 via inlet 1008. The air from inlet 1008 is compressed by ROOTS-type blower 1002, and then passed to the patient and/or other sections of the mechanical ventilator through outlet 1010. Fluid communication paths are provided from the input of ROOTS-type blower 1002 to solenoid valve 1012, and from the output of ROOTS-type blower 1002 to solenoid valve 1014. Ambient air pressure is also channeled to solenoid valves 1012 and 1014 via ambient inlets 1016 and 1018, respectively.

The output fluid communication channels of solenoid valves 1012 and 1014 are provided to blower differential pressure transducer 1040 to convert the pressure differential between the two channels into an electrical signal representative of that pressure differential. During normal operation, transducer 1040 measures the difference between the output pressure and input pressure of ROOTS-type blower 1002. By controlling solenoid valves 1012 and 1014, transducer 1040 can also measure the pressure difference between the two ambient pressure inlets during an "auto-zero" phase of transducer 1040. Processor 1020 provides control of solenoid valves 1012 and 1014, with solenoid drivers 1032 transforming the digital control signals from processor 1020 into power DC signals capable of driving the solenoid valves. Absolute pressure transducer 1022 and temperature transducer 1024 generate electrical signals representing the absolute pressure level and the temperature. Each of transducers 1022, 1024 and 1040 are coupled to transducer (XDCR) interface block 1026, which may provide signal amplification and filtering of the analog signals that are then provided to A/D (analog-to-digital) converter circuit 1038. A/D converter 1038 transforms the analog signals into digital values that may be processed by processor 1020.

In addition to A/D converter circuit 1038, Processor 1020 also has the following associated circuitry: flash memory 1048, JTAG test circuitry 1046, random access memory (RAM) 1044, and UARTs (universal asynchronous receiver-transmitters) 1042 and 1036. External JTAG connector 1050 is coupled to JTAG circuit 1046 to facilitate hardware tests and debugging in accordance with the JTAG standard. Telemetry connector 1052 is coupled to UART 1042 for the transmission of measured ventilator parameters to a remote system, e.g., for monitoring purposes. Communication and power connector 1054 is coupled to UART 1036 for facilitating further external communication with the ventilator system, e.g., for operational testing and control. Connector 1054 also provides any necessary power signals to the motor/compressor system (e.g., 3.3, 5.0 and/or 15 VDC (volts DC)).

Analog sensors 1006 (e.g., analog Hall effect sensors) are arranged on a PC board in a circular pattern perpendicular to the rotor shaft of BLDC motor 1004 and adjacent to a two-pole magnet attached to the end of the rotor shaft. Analog sensors 1006 provide measurements needed for computation of BLDC rotor position. The analog outputs of sensors 1006 are passed through sensor interface 1028 (e.g., for amplification and filtering), and then into A/D converter circuit 1038, where the analog sensor signals are converted into digital values for processing within processor 1020.

Processor 1020 executes software instructions to implement certain elements of the motor/compressor control loop. Processor 1020 may be implemented, for example, with a general purpose processor or with a digital signal processor (DSP). Other embodiments may implement the functionality of processor 1020 in firmware (e.g., instructions stored in an EPROM) or as equivalent logic in a hardware device (e.g., an ASIC (application specific integrated circuit) or an FPGA (field programmable gate array)).

Processor 1020 receives the digitized sensor signals and pressure measurements via A/D converter block 1038 (values may use RAM 1044 for temporary storage), and determines an appropriate speed control value based upon the control process implemented (e.g., pressure control or volume control). Processor 1020 also generates the appropriate commutation control signals given the current commutation state, and modulates the pulse widths of those commutation control signals based on the speed control value. The modulated commutation control signals are provided to three phase inverter 1030.

Three-phase inverter 1030 generates drive signals for the individual stator coils in BLDC motor 1004, as previously described. The system may also include a current limit circuit 1034 coupled to three-phase inverter block 1030.

Figure 11:
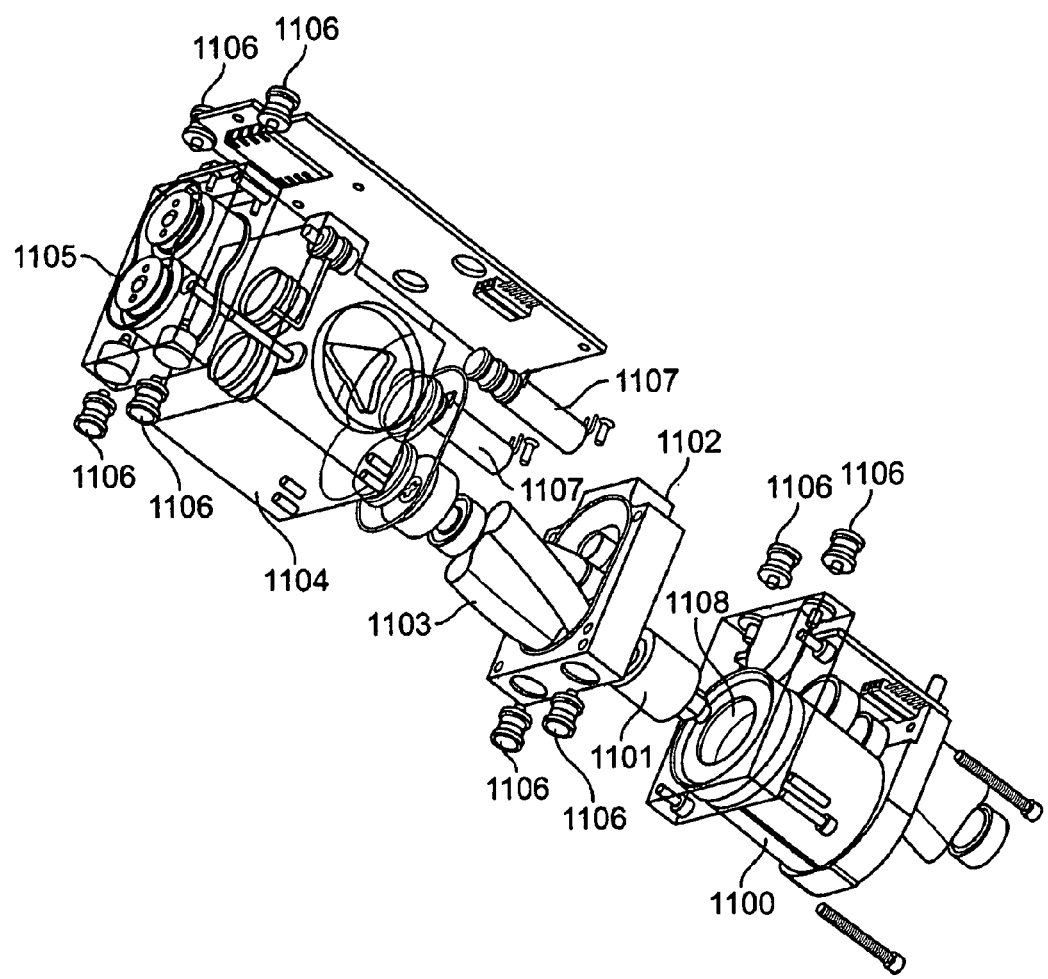
FIG. 11 is an exploded view of a blower assembly in accordance with one or more embodiments of the invention.

FIG. 11 is an exploded view of the physical structure of a ROOTS-type blower, in accordance with an embodiment of the invention. As shown, structure 1100 includes the BLDC motor. The stator of the BLDC motor surrounds hollow bore 1108, into which a rotor 1101 is inserted during manufacturing. Rotor 1101 spins under the influence of the energized stator coils within the BLDC motor. Stabilizer 1102 supports the rotating axis shared by rotor 1101 and ROOTS-type blower impeller 1103. The shared axis forces impeller 1103 to rotate when the BLDC motor forces rotor 1101 to rotate.

Impeller 1103 rotates within ROOTS-type blower housing 1104, with one end of the impeller axis coupled to gears 1105. A second impeller (not shown) is also coupled to gears 1105 such that the second impeller rotates in the opposite direction of impeller 1103. During operation, the rotation of the impellers forces air to flow between the impellers with additional energy, creating pressure. Openings in either side of housing 1104 provide the air input and output paths.

As shown, the elements of the blower assembly are coupled to surrounding structures in the lateral direction by broad connectors 1106, and in the longitudinal direction by long connectors 1107. The increased size of those connectors provides greater support for the apparatus, while providing dampening of vibrations due to the motion of the blower apparatus.

Figure 12:
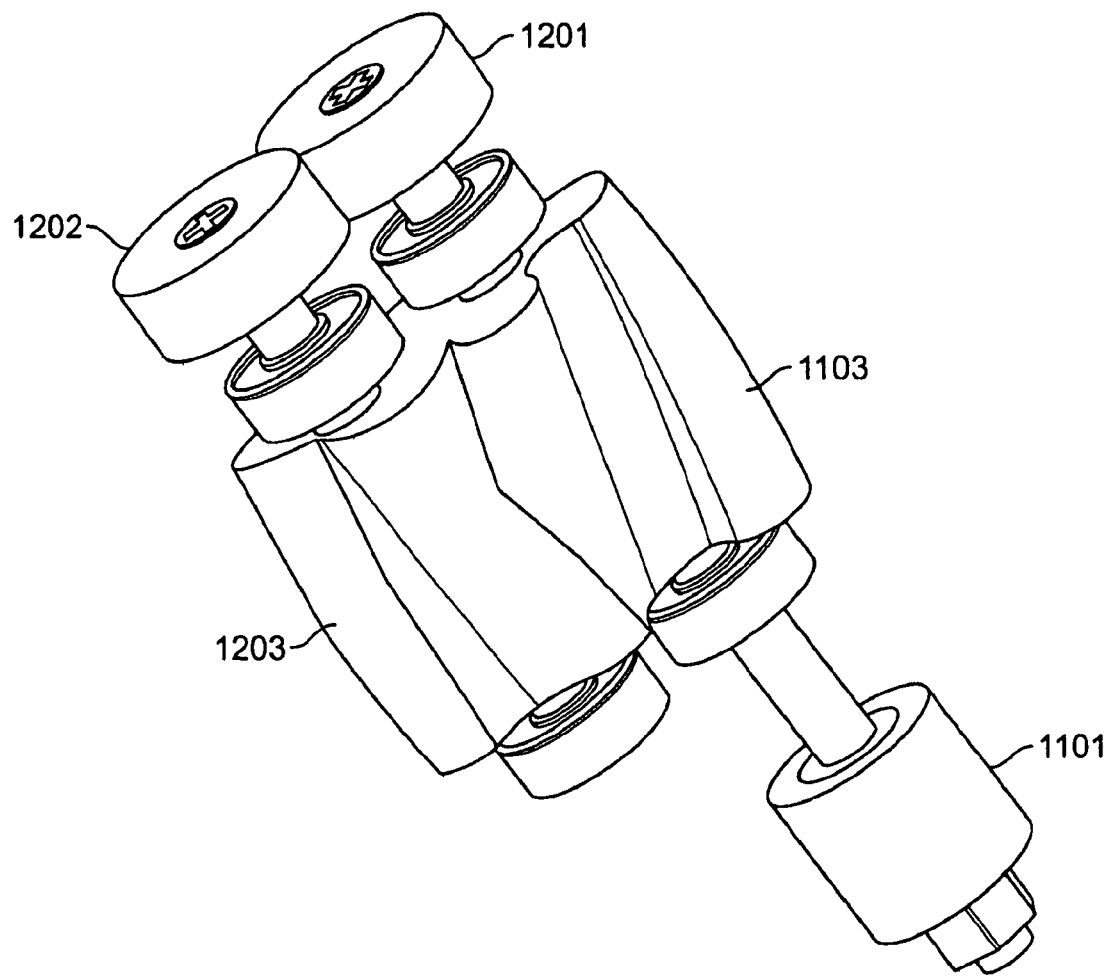
FIG. 12 is a perspective view of a pair of ROOTS-type blower impellers in accordance with one or more embodiments of the invention.

FIG. 12 illustrates the interlocking nature of the ROOTS-type blower impellers 1103 and 1203. The shared axis of impeller 1103 and rotor 1101 is visible in this image, showing the mechanism by which the ROOTS-type blower impellers are driven. Engagement of gears 1201 and 1202 provides the transfer of opposing rotational energy from the axis of impeller 1103 to the axis of impeller 1203.

V. Noise Reduction

Because ROOTS-type blowers are relatively noisy, and because embodiments of the invention are designed for use in close proximity to the patient, one or more methods and features for dampening the noise generated by the blower may be implemented in embodiments of the invention. Such methods and features may include forming the blower rotors with a helical twist (as shown in FIG. 12), and using multiple sound muffling techniques, such as the anti-noise cancellation methods described previously.

Additionally, embodiments of the invention may include the use of perforated tube mufflers, in which numerous perforations protrude from the body of each perforated tube at right angles in the form of small tubes, creating a longer effective muffling pathway capable of efficiently attenuating sound waves without concomitant increase in muffler weight and size. The perforated tube mufflers are preferably constructed of a lightweight polymer or other sturdy but lightweight material.

Figure 13A:
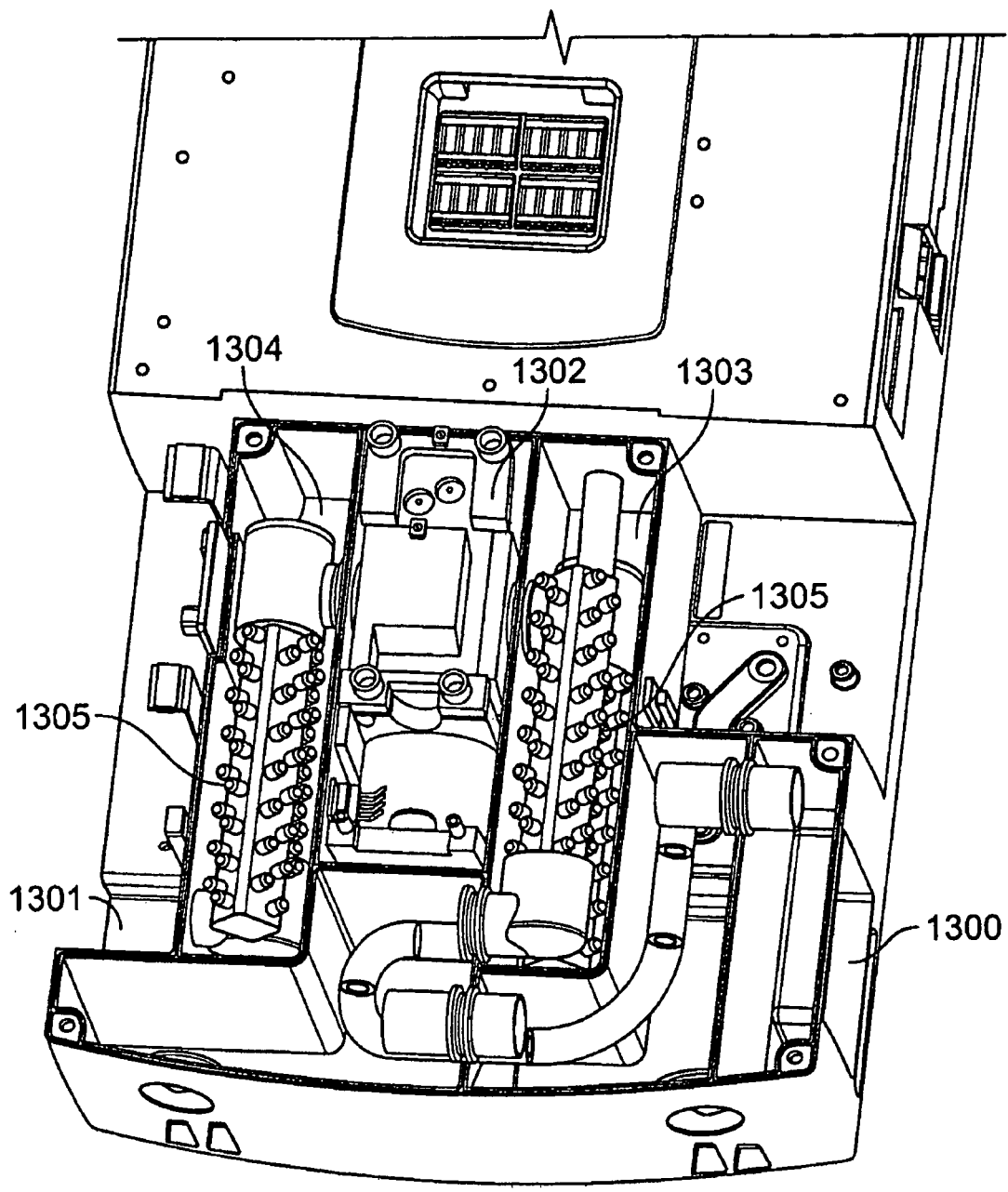
FIGS. 13A and 13B are views of a ventilator apparatus having silencer chambers with perforated tubes, in accordance with one or more embodiments of the invention.

FIG. 13A shows a view of the pneumatic pathways and noise reduction chambers of one embodiment of the invention. As shown, air enters the ventilator through filtered inlet 1300, and traverses a twisted pneumatic path until it reaches the bottom of silencer chamber 1303. Near the top of silencer chamber 1303, the air is directed into an inlet port of the Roots ROOTS-type blower assembly 1302. The compressed air is output from the ROOTS-type blower assembly into the upper portion of silencer chamber 1304, and then directed on from the bottom (1301) of chamber 1304.

Figure 13B:
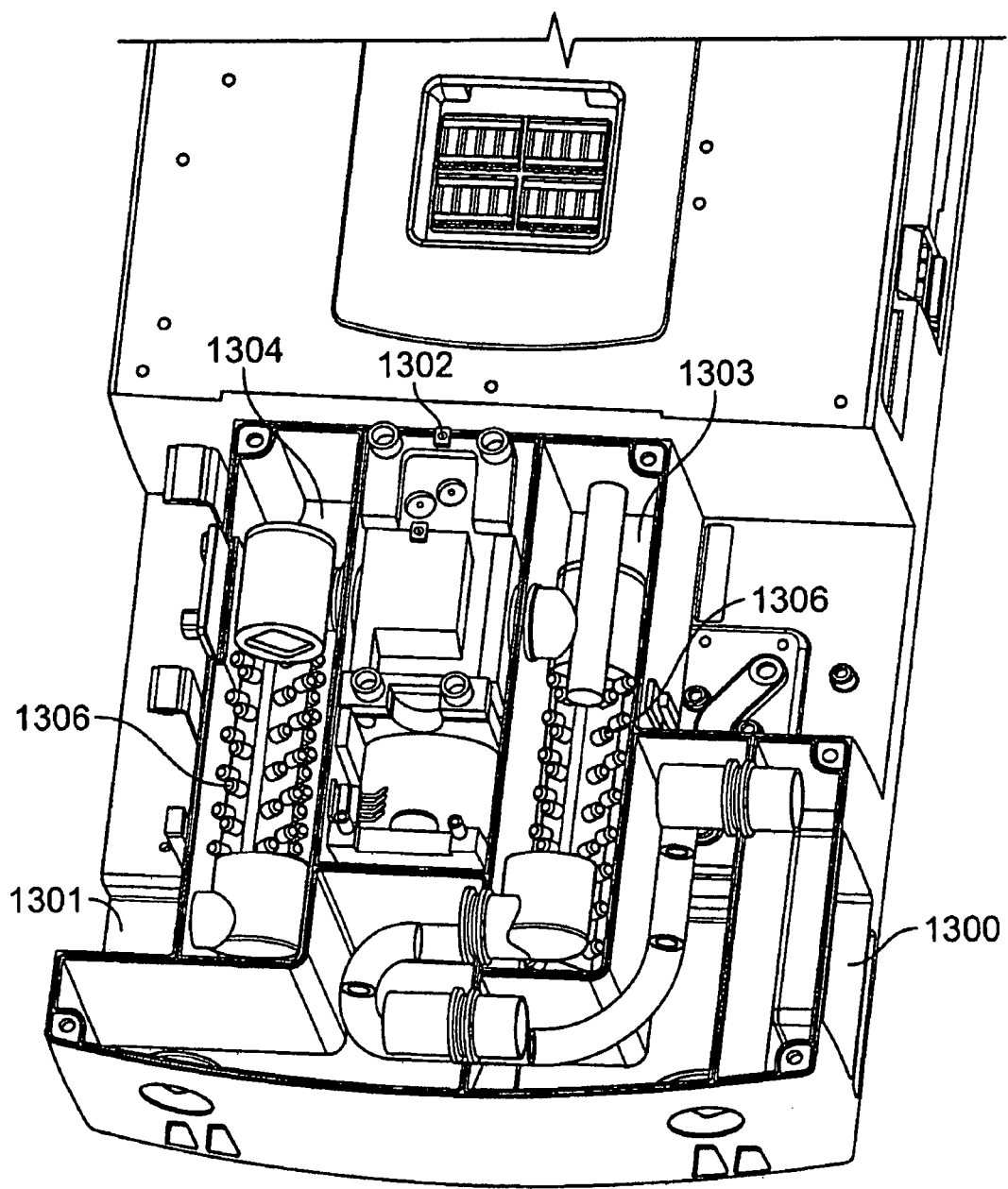

Silencer chambers 1303 and 1304 each include two perforated muffler tubes 1305 and 1306 positioned in parallel, e.g., with one above the other. FIG. 13B illustrates the silencer chambers with the top tube (1305) removed, providing a clearer view of underlying tube 1306. The input to each silencer chamber is through one end of tube 1305, with the exit being through the opposing end of tube 1306. The air must therefore flow out of tube 1305 and in through tube 1306. The pressure transients associated with compressor noise are dampened by the resistance presented by the small tubular perforations. Further, the coherence of the noise pressure waves is disrupted by the forced traversal of multiple small pathways of varying lengths. The varying length pathways cause the air flow of the respective pathways to recombine out of phase with each other, diffusing the previously coherent noise. As a result, much of the compressor noise is attenuated during transit of the silencer chambers.

Embodiments of the invention may also include graduated slots in the housing of the Roots blower which permit a smooth, gradual backflow of gas as the leading edge of the blower rotors approach the blower outlet port, thus reducing the typical Roots blower pulsing effect responsible for much of the noise. The graduated slots in the housing of the Roots blower maximize noise reduction while minimizing the reduction in efficiency attendant upon permitting gradual backflow into the blower chambers during rotation.

Figure 14A:
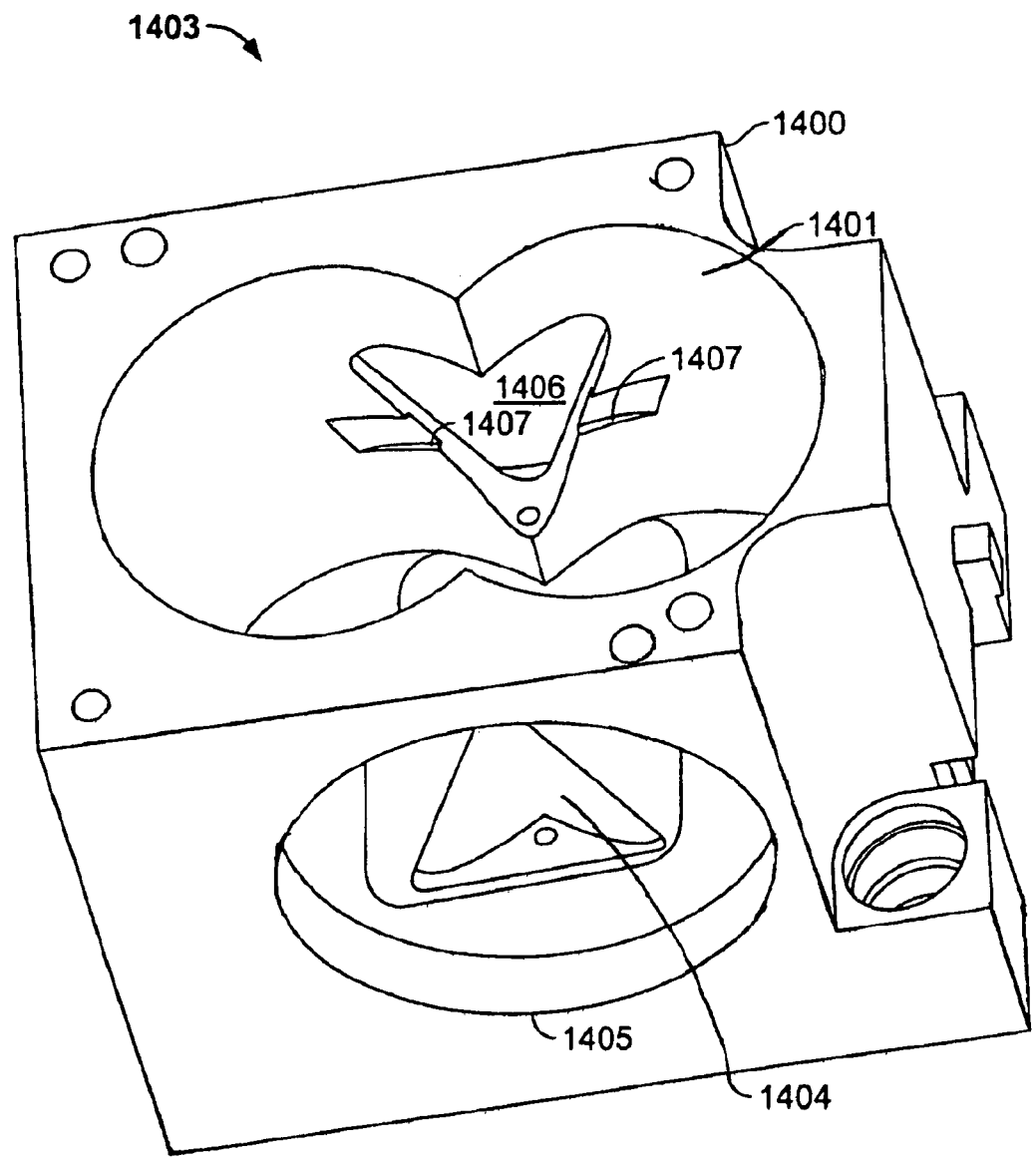
FIGS. 14A through 14D are various views of a ROOTS-type blower housing, illustrating graduated slots at the air outlets, in accordance with one or more embodiments of the invention.
Figure 14B:
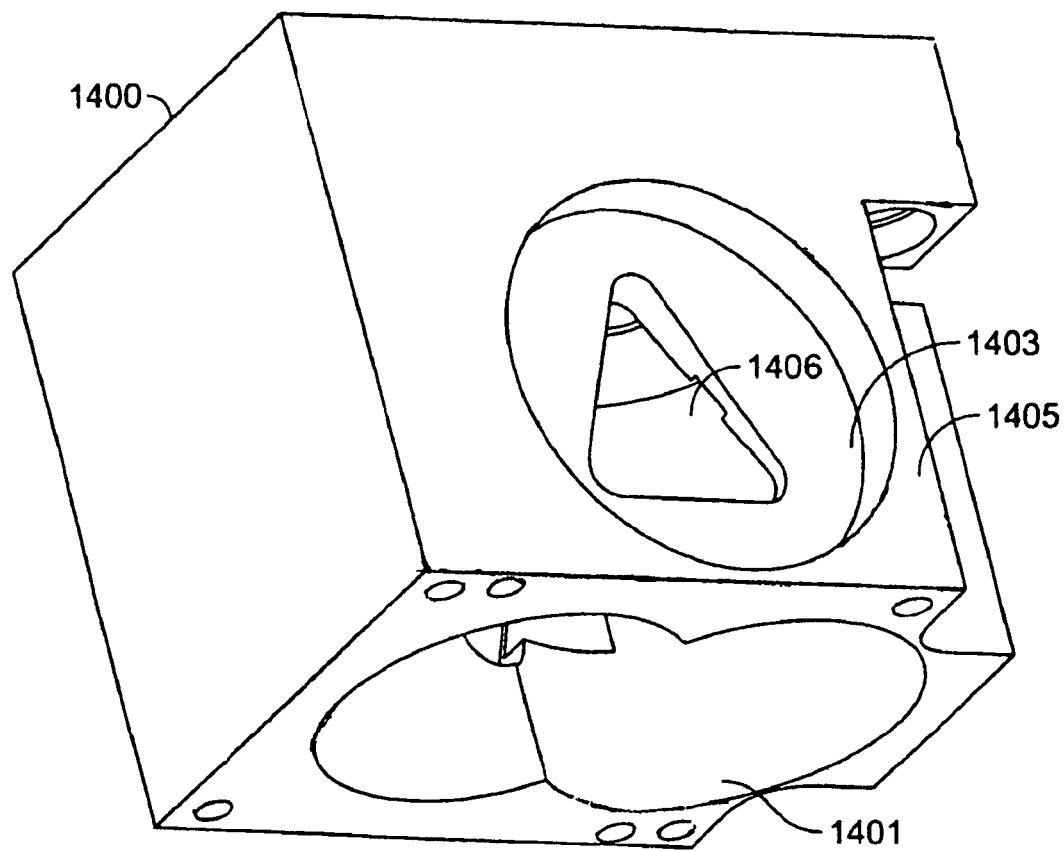
Figure 14C:
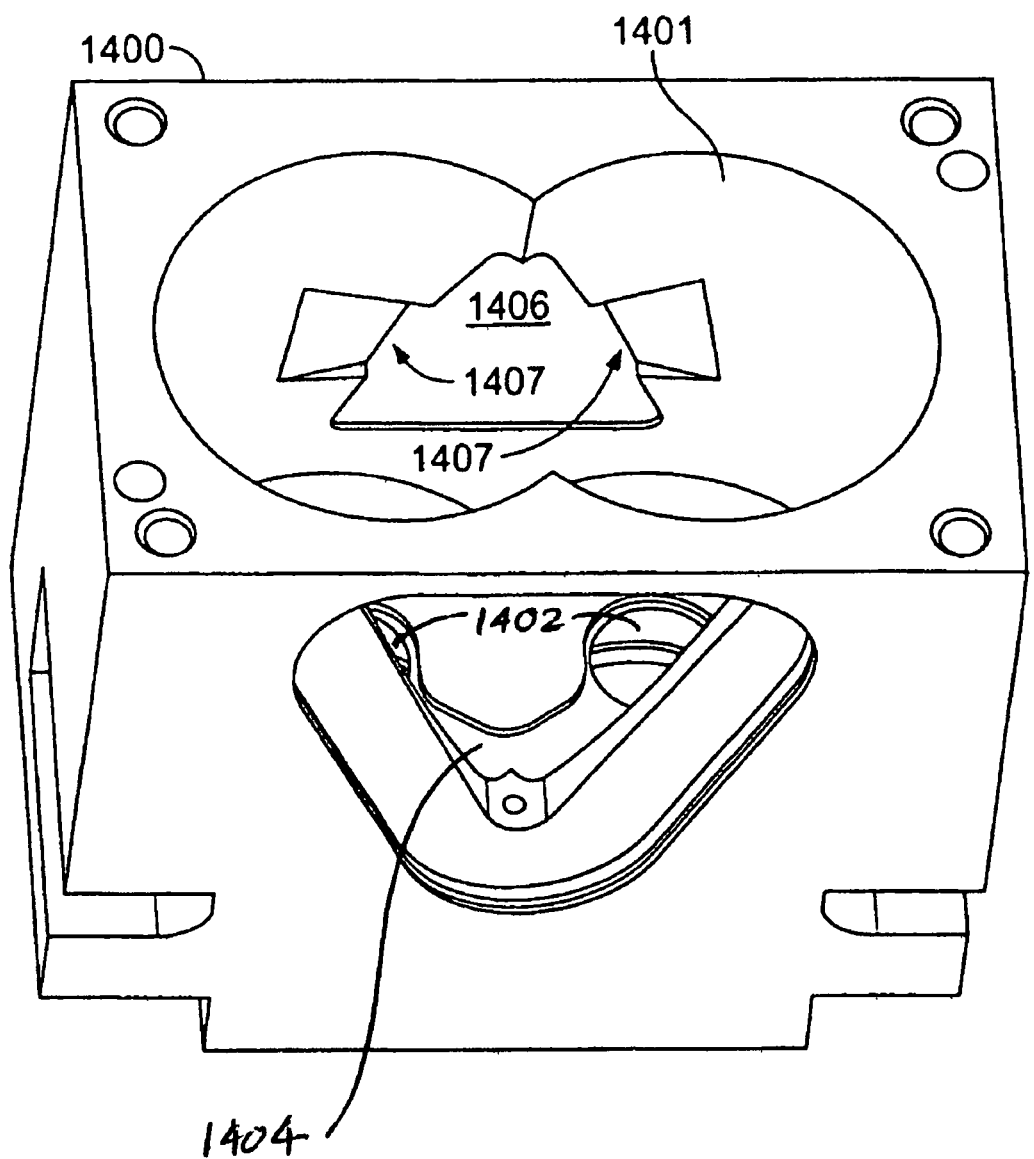
Figure 14D:
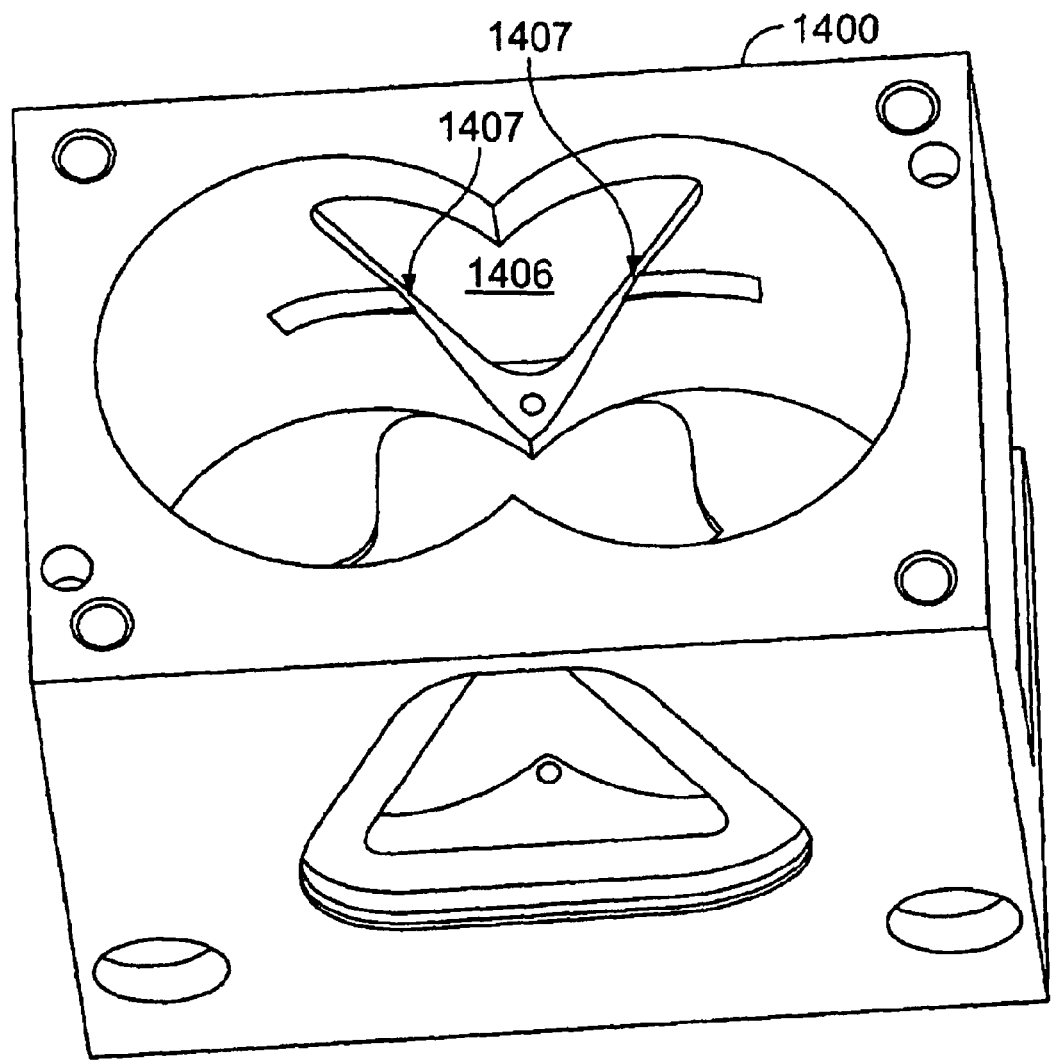

FIGS. 14A 14D provide different views of the Roots blower housing 1400. Orifice 1401 faces the direction of the BLDC motor, and receives the pair of impellers. In the opposing face 1402 of housing 1400, two orifices are provided through which the axes of the impellers extend to engage gear structure 1105 perpendicular to the axis defined by orifice 1401 and opposing face 1402, an air inlet 1403 and a compressed air output port 1404 are provided. The inlet and output ports are configured with an initial circular indentation 1405, e.g., to receive a tubular air guide apparatus. Within the circular indentation is an orifice 1406 having a roughly triangular cross-section at the level of indentation 1405, and a curved wing-shape where the triangular cut-out meets the dual-rounded chamber encompassing the rotating impellers. Also, a groove 1407 is formed on the inside of orifice 1406 roughly midway along the side of the triangle, aligned in the same plane as the stacking of the impellers. Grooves 1407 are deepest at the edge of triangular orifice 1406, and gradually diminish to the level of the inner chamber away from orifice 1406.

The above techniques, methods and features reduce the noise commonly associated with Roots blowers, minimizing any auditory discomfort to the patient, thus permitting the ventilator device to be used in close proximity to a patient without adding significantly to the weight or dimensions of embodiments of the invention, and thereby facilitating portability.

The employment in the ventilator of a Roots blower, in combination with the noise reduction techniques described above, permits improved miniaturization of the ventilator heretofore unachievable without sacrificing sophisticated ventilation modes or patient comfort.

Thus, a portable ventilator has been described. Particular embodiments described herein are illustrative only and should not limit the present invention thereby. The invention is defined by the claims and their full scope of equivalents.

What is claimed is:

1. A portable ventilator comprising:
   a blower unit outputting compressed gas and including interlocking helical lobed impellers counter-rotatable within a blower housing in variable speed mode;
   a speed servo configured to change a speed of the interlocking helical lobed impellers of the blower unit to accelerate and decelerate the blower unit to provide ventilation; and
   an exhalation servo control system configured to provide a desired positive end expiratory pressure from the output of said blower unit.

2. The portable ventilator of claim 1, further comprising a ventilator control system comprising a plurality of processors including a ventilator processor operative to alternately accelerate and decelerate the blower unit to effect inspiration and permit exhalation.

3. The portable ventilator of claim 2, wherein the ventilator control system further comprises at least one of a blower processor, an exhalation processor, a blender processor, and a pressure processor.

4. The portable ventilator of claim 3, wherein:
   each processor is operative to communicate with the ventilator processor,
   the blower processor being operative to control operation of the blower unit,
   the exhalation processor being operative to control actuation of an exhalation control valve,
   the blender processor being operative to regulate oxygen concentration in gas delivered outside the blower housing, and
   the pressure processor being operative to monitor pressure at least one transducer disposed within the portable ventilator.

5. The portable ventilator of claim 1 further comprising an integration of the blower unit and speed servo with at least one of a transducer module, an exhalation control module and a blender module.

6. The portable ventilator of claim 5, wherein:
   the exhalation module being operative to control actuation of an exhalation control valve,
   the blender module being operative to regulate oxygen concentration in the delivered gas, and
   the pressure module being operative to monitor pressure in the transducers.

7. The portable ventilator of claim 6 wherein:
   the ventilator control system includes at least one of a blower processor, an exhalation processor, a blender processor, and a pressure processor,
   each processor communicating with the ventilator processor,
   the blower processor controlling operation of the blower unit;
   the exhalation processor controlling actuation of an exhalation control valve,
   the blender processor regulating oxygen concentration in gas provided externally, and
   the pressure processor monitoring at least one transducer disposed within the portable ventilator.

8. The portable ventilator of claim 1, further comprising:
   a motor driving the blower unit; and
   a blower processor controlling operation of the blower unit, wherein the blower processor provides control signals to the motor based on at least one of the following: characterization data for the blower, and a measurement of gas flow generated by the blower unit.

9. A portable ventilator comprising:
a blower unit having interlocking helical lobed impellers counter-rotatable within a blower housing at a varying speed, said blower unit providing compressed gas for providing ventilation;
a speed servo coupled to the blower unit and configured to maintain a speed of the blower unit at a substantially constant speed to provide a desired flow rate; and
an exhalation servo control system configured to close an output valve during an exhalation phase of the ventilation.

10. A portable ventilator, comprising:
a blower unit having interlocking helical lobed impellers counter-rotatable within a blower housing for providing gas flow; and a pressure transducer module monitoring pressure transducers of the portable ventilator, an exhalation control module controlling actuation of an exhalation control valve; a blender module regulating oxygen concentration in gas delivered; and a blower module controlling operation of the blower unit, wherein the blower module is communicatively coupled to the blower unit and configured to control a speed of the blower unit.

11. An apparatus, comprising:
a first unit drawing gas through an inlet unit and delivering pressurized gas through an inspiratory port, the gas being pressurized by interlocking helical lobed impellers of a compressor unit, the compressor unit supporting both single limb and dual limb patient circuits, accommodating an exhalation valve being implemented either externally or internally with respect to a ventilator enclosure;
a second unit with an exhalation control port and PEEP (positive end-expiratory pressure) control generate a pilot pressure that closes exhalation valve during inspiration and opens it against a software controlled PEEP pilot pressure during exhalation, with the software being stored in a memory unit;
a first processor controlling a speed of the interlocking helical lobed impellers of the first unit;
a second processor, separate from the first processor, controlling the second unit; and
a third processor, separate from the first and second processors, being in communication with both first and second processor.

12. The apparatus of claim 11, further comprising a scavenging port recycling the compressed gas that is not used during exhalation.

13. The apparatus of claim 11, further comprising a blender unit delivering blended gas to the compressor unit.

14. The apparatus of claim 11, wherein the blended gas delivery in an inspiratory limb being monitored via an external sensor coupled to an interface of the blender unit, and displayed on a user interface.

15. The apparatus of claim 14, further comprising a second sensor monitoring blood oxygen level, coupled to an internal pulse oximeter, and displayed on the user interface.

16. The apparatus of claim 11, wherein the first, second units and the first, second and third processors are integrated into a single unit.

17. A method, comprising:
outputting compressed gas with interlocking helical lobed impellers counter-rotatable in a variable speed mode or a constant speed mode by a first unit;
changing, by a processor, a speed of the interlocking lobed impellers to provide ventilation by a second unit; and
providing a desired positive end expiratory pressure from the output of the compressed gas by a third unit.

18. The method of claim 17, further comprising controlling with a plurality of processors including a ventilator processor alternately accelerate and decelerate the compressed gas to effect inspiration and permit exhalation.

19. The method of claim 17, wherein controlling with the plurality of processors including at least one of a blower processor, an exhalation processor, a blender processor, and a pressure processor.

20. The method of claim 17, wherein:
communicating from each processor with a main processor,
controlling with the blower processor the operation of the compressed gas,
controlling actuation of an exhalation control valve by the exhalation processor,
regulating oxygen concentration in gas delivered by the blender processor, and
monitoring pressure with at least one transducer by the pressure processor.

21. The method of claim 17, further comprising an integrating the first, second and third unit into a single unit, with each unit being controlled separately and in communication with each other.

22. The method of claim 21, further comprising:
controlling actuation of an exhalation control valve by a fourth unit;
regulating oxygen concentration in the delivered gas by a fifth unit; and
monitoring pressure in the transducers by a sixth unit.

23. The method of claim 22, wherein:
the fourth, fifth and sixth units being integrated into the single unit with the first, second and third units;
the fourth, fifth and sixth units being controlled separately from each other and in communication with each other; and
the first unit supports both single limb and dual limb patient circuits, accommodating an exhalation valve being implemented either externally or internally with respect to a ventilator enclosure.

24. A portable ventilator, comprising:
a means for outputting compressed gas and including interlocking helical lobed impellers counter-rotatable within a blower housing in variable speed mode;
a means for accelerating and decelerating the interlocking helical lobed impellers of the means for outputting compressed gas to provide ventilation;
a means for providing a desired positive end expiratory pressure from the output of the means for outputting compressed gas; and
a means for controlling the ventilator comprising a plurality of processors including a ventilator processor operative to alternately accelerate and decelerate the means for outputting compressed gas to effect inspiration and permit exhalation within the blower housing.

* * * * *